US00RE48165E

(19) United States
(12) Reissued Patent
Ignatyev et al.

(10) Patent Number: US RE48,165 E
(45) Date of Reissued Patent: Aug. 18, 2020

(54) ALKENYL (PERFLUOROALKYL) PHOSPHINIC ACIDS

(71) Applicant: Merck Patent GmbH, Darmstadt (DE)

(72) Inventors: Nikolai (Mykola) Ignatyev, Duisburg (DE); Michael Schulte, Bischofsheim (DE); Karsten Koppe, Marl-Polsum (DE); Vural Bilir, Duesseldorf (DE); Walter Frank, Wuppertal (DE)

(73) Assignee: Merck Patent GmbH, Darmstadt (DE)

(21) Appl. No.: 16/289,925

(22) Filed: Mar. 1, 2019

Related U.S. Patent Documents

Reissue of:

(64) Patent No.: 10,160,777
Issued: Dec. 25, 2018
Appl. No.: 15/519,657
PCT Filed: Sep. 25, 2015
PCT No.: PCT/EP2015/001911
§ 371 (c)(1),
(2) Date: Apr. 17, 2017
PCT Pub. No.: WO2016/058668
PCT Pub. Date: Apr. 21, 2016

(30) Foreign Application Priority Data

Oct. 17, 2014 (EP) ..... 14003549

(51) Int. Cl.

| | |
|---|---|
| ***C07F 9/30*** | (2006.01) |
| ***B01J 41/13*** | (2017.01) |
| ***B01J 20/10*** | (2006.01) |
| ***B01J 20/22*** | (2006.01) |
| ***B01J 20/28*** | (2006.01) |
| ***B01J 20/30*** | (2006.01) |
| ***B01J 20/32*** | (2006.01) |
| ***B01J 41/04*** | (2017.01) |
| ***C07F 9/53*** | (2006.01) |
| ***C08F 112/14*** | (2006.01) |
| ***C08F 230/02*** | (2006.01) |
| ***C08F 114/18*** | (2006.01) |
| ***C08F 130/02*** | (2006.01) |
| ***C08F 214/18*** | (2006.01) |
| ***C08F 261/06*** | (2006.01) |
| ***C22B 3/38*** | (2006.01) |
| ***C22B 3/24*** | (2006.01) |
| ***C22B 59/00*** | (2006.01) |

(52) U.S. Cl.
CPC ..... *C07F 9/302* (2013.01); *B01J 20/103* (2013.01); *B01J 20/22* (2013.01); *B01J 20/28047* (2013.01); *B01J 20/3085* (2013.01); *B01J 20/3204* (2013.01); *B01J 20/3265* (2013.01); *B01J 41/04* (2013.01); *B01J 41/13* (2017.01); *C07F 9/304* (2013.01); *C07F 9/5316* (2013.01); *C08F 112/14* (2013.01); *C08F 114/18* (2013.01); *C08F 130/02* (2013.01); *C08F 214/18* (2013.01); *C08F 230/02* (2013.01); *C08F 261/06* (2013.01); *C22B 3/0064* (2013.01); *C22B 3/24* (2013.01); *C22B 59/00* (2013.01); *Y02P 10/234* (2015.11)

(58) Field of Classification Search
CPC ..... C07F 9/302; C07F 9/5316; C07F 9/304; C08F 230/02; C08F 130/02; C08F 114/18; C08F 214/18; C08F 261/06; C08F 112/14; C08F 30/02; C22B 59/00; C22B 3/0064; C22B 3/24; B01J 41/04; B01J 20/3265; B01J 20/3204; B01J 20/3085; B01J 20/28047; B01J 20/22; B01J 20/103; B01J 41/13; Y02P 10/234
See application file for complete search history.

(56) References Cited

U.S. PATENT DOCUMENTS

| | | | | |
|---|---|---|---|---|
| 4,647,438 | A | 3/1987 | Sabot et al. | C01F 17/10 423/21.5 |
| 7,691,478 | B2 | 4/2010 | Avaltroni et al. | |
| 8,962,892 | B2 | 2/2015 | Ignatyev et al. | |
| 9,346,838 | B2 | 5/2016 | Ignatyev et al. | |
| 2003/0189193 | A1 | 10/2003 | Mininni et al. | |
| 2003/0194162 | A1 | 10/2003 | Mininni et al. | |
| 2012/0330063 | A1 | 12/2012 | Ignatyev et al. | |
| 2015/0141698 | A1 | 5/2015 | Ignatyev et al. | |

FOREIGN PATENT DOCUMENTS

| | | | |
|---|---|---|---|
| FR | 2267380 | A1 | 11/1975 |
| WO | 03082884 | A1 | 10/2003 |
| WO | 2011/110281 | A1 | 9/2011 |
| WO | 2014/005668 | A1 | 1/2014 |

OTHER PUBLICATIONS

Examination report in Indian Application No. 201737016923 dated Oct. 15, 2019 (pp. 1-5).

International Search Report dated Dec. 2, 2015 issued in corresponding PCT/EP2015/001911 application (2 pages).

D.F. Peppard et al., "DI n-Octyl Phosphinic Acid as a Selective Extractant for Metallic Cations", Journal of Inorganic and Nuclear Chemistry, vol. 27, No. 9 (1965) pp. 2065-2073.

L.M. Yagupol'skii et al., "Arylbis (HeptaFluoropropyl) Phosphine Oxides, Electronic Nature of the P (O) (C9F7)2 Group", J. Gen. Chem. U.S.S.R. Engl. Transl., vol. 54 (1984) pp. 297-302.

A.I. Hosein et al., "A Study of the Reaction of Perfluoroalkyl Grignard Reagents With Phosphoryl Chloride and Phenylphosphonic Dichloride", Dalton Transactions, vol. 41 (2012) pp. 13504-13508.

J.E. Griffiths et al., "Oxygen Chemistry of the (CF3)2P Group: The Diphosphoxane; The Phosphinous Acid, Esters and Related Phosphine Oxides; Phosphinyl Halides and Infrared Spectra", J. Am. Chem. Soc., vol. 84 (1962) pp. 3442-3450.

(Continued)

*Primary Examiner* — Jerry D Johnson

(74) *Attorney, Agent, or Firm* — Millen White Zelano and Branigan, PC; John Sopp

(57) ABSTRACT

The invention relates to alkenyl(perfluoroalkyl)phosphinic acids, to the preparation and intermediates thereof, to the use thereof as monomers for the preparation of oligomers and/or polymers, to the corresponding oligomers/polymers, to the corresponding support materials comprising the oligomers/polymers, and to the use thereof as ion exchangers, as catalysts or extraction medium and corresponding salts thereof.

20 Claims, No Drawings

(56) References Cited

OTHER PUBLICATIONS

L.D. Quin et al., "Optically Active Phosphorus Compounds From Transformations of Other P-Chiral Precursors and From Asymmetric Synthesis Methods", A Guide to Organophosphorus Chemistry (2000) pp. 282-306.

N.V. Pavlenko et al., "Reaction of Tris(Perfluoroalkyl)Difluorophosphoranes With Organolithium Compounds", J. Gen. Chem. U.S.S.R. Engl. Transl., vol. 57 (1987) pp. 99-102.

ALKENYL (PERFLUOROALKYL) PHOSPHINIC ACIDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The invention relates to alkenyl(perfluoroalkyl)phosphinic acids, to the preparation and intermediates thereof, to the use thereof as monomers for the preparation of oligomers and/or polymers, to the corresponding oligomers/polymers, and to the use thereof as ion exchangers, catalysts, extraction media and the corresponding salts.

A multiplicity of symmetrical bis(perfluoroalkyl)phosphinic acids is known for a wide variety of uses. Peppard, D. F. et al., Journal of Inorganic and Nuclear Chemistry 1965, 27(9), 2065-73, describe, for example, the use of bis(n-octyl)phosphinic acid as selective extractant for metallic cations.

The only examples of classes of asymmetrical phosphinic acids containing perfluorinated groups are aryl(perfluoroalkyl)phosphinic acids, $R^F$(aryl)-P(O)OH (aryl=3-$C_6H_4F$, 4-$C_6H_4F$ or $C_6H_5$ and $R^F$=$C_3F_7$[L. M. Yagu-pol'skii, N. V. Pavlenko, N. V. Ignat'ev, G. I. Matyushecheva, V. Y. Semenii, J. Gen. Chem. U.S.S.R. Engl. Transl. 1984, 54, 297-302] or aryl=$C_6H_5$ and $R^F$=$C_nF_{2n+1}$ (n=2, 4, 6, or 8) [A. I. Hosein, A. J. M. Caffyn, Dalton Trans. 2012, 41, 13504-13508]) or asymmetrical phosphinic acids containing two different perfluoroalkyl groups [WO 2003/082884].

A multistep procedure has been used for the preparation of aryl(perfluoroalkyl)phosphinic acids. Aryl(heptafluoropropyl)phosphinic acids have been obtained by hydrolysis of aryl[bis(heptafluoropropyl)]phosphine oxides using aqueous sodium carbonate solution. The aryl[bis(heptafluoropropyl)]-phosphine oxides themselves have been prepared using a multistep procedure beginning with the reaction of bis(heptafluoropropyl)chlorophosphine, $(C_3F_7)_2PCl$ (a non-commercially available substance), with arylmagnesium bromides, followed by chlorination to give $XC_6H_4$; $(C_3F_7)_2PCl_2$ and hydrolysis using formic acid to give $XC_6H_4(C_3F_7)_2P{=}O$ (X=H or F). This complex procedure is not suitable for the preparation of large amounts of aryl(perfluoroalkyl) phosphinic acids.

The phosphine oxides of the type $R(CF_3)_2P{=}O$ with mixed substituents have been obtained by an Arbuzov-type rearrangement of bis(trifluoromethyl)phosphinous acid esters, $(CF_3)_2P{-}OR$, under the action of $CH_3I$ [J. F. Griffiths, A. B. Burg, J. Am. Chem. Soc. 1962, 84, 3442-3450].

WO 2003/082884 describes the preparation of asymmetrical bis(perfluoroalkyl)phosphinic acids by reaction of a perfluoroalkylphosphonic acid dichloride ($R_fP(O)Cl_2$) with perfluoroalkylmagnesium bromide to give an asymmetrically substituted bis(perfluoroalkyl)phosphinic acid chloride and subsequent hydrolysis to give the acid.

Corresponding asymmetrical alkenylperfluoroalkylphosphinic acids are, by contrast, not known compounds, even though unfluorinated asymmetrical phosphine oxides and asymmetrical dialkylphosphinic acids and dialkylphosphinic acid derivatives are typical reagents (ligands) for asymmetrical synthesis [L. D. Quin, G. S. Quin, A Guide To Organophosphorus Chemistry, Wiley-Interscience, 2000, 282-306].

U.S. Pat. No. 4,647,438 describes a process for the liquid-liquid extraction of rare-earth metals from aqueous solutions by an extraction medium comprising an organic phosphinic acid of the formula R1(R2)P(O)(OX), where R1 and R2 may be identical or different and denote unsubstituted or substituted alkyl, cycloalkyl, alkoxyalkyl or alkylcycloalkyl and X denotes H or a cation. Possible substituents of the alkyl group are described as being OH or halogen atoms, for example F or Cl. R1 and R2 are preferably described as linear or branched alkyl group having at least 6 C atoms or as cycloalkyl group having at least 6 C atoms. An asymmetrical phosphinic acid mentioned is 2,4,4-trimethylpentylcyclohexylphosphinic acid. No fluorinated or perfluorinated phosphinic acids are described. In the examples, bis(2,4,4-trimethylpentyl)phosphinic acid is used.

U.S. Pat. No. 7,691,478 describes thin films comprising, for example, a phosphinic acid, where the phosphinic acid is bonded to the substrate via the acid function. Diphenylphosphinic acid, phenylphosphinic acid and bis(perfluoroheptyl) phosphinic acid are described as representative. In Example 1, no phosphinic acid is used.

The object of the invention was the broadening of the range available to the person skilled in the art of polymerisable monomers which are suitable for the preparation of oligomers and polymers, and which have the functionality of a strong Brønsted acid. Both the monomers and also the corresponding oligomers/polymers are therefore suitable as ion exchanger or as extraction medium or as Brønsted acid catalysts and can be combined with a suitable support material. Further advantages of the present invention arise for the person skilled in the art from the following disclosure.

Surprisingly, the alkenyl(perfluoroalkyl)phosphinic acids of the formula I according to the invention achieve the object set in an excellent manner.

The invention accordingly relates firstly to the compounds of the formula I,

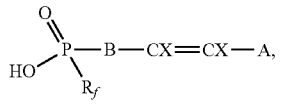

I where $R_f$ denotes a straight-chain or branched perfluoroalkyl group having 1 to 12 C atoms, A denotes H, F, Cl or a straight-chain or branched alkyl group having 1 to 12 C atoms, B denotes $-(CR_1R_2)_n-$, $[-(CR_1R_2)_m-O-(CR_1R_2)_{m1}-]_{m2}$, arylene or substituted arylene, X denotes H, F and/or Cl, n denotes an integer from 0 to 20, m denotes an integer from 1 to 20, $m_1$ denotes an integer from 0 to 8, $m_2$ denotes an integer from 1 to 20 and $R_1$ or $R_2$ each, independently of one another, denote H, F, Cl or a straight-chain or branched alkyl group having 1 to 12 C atoms.

$R_1$ and $R_2$ may be identical or different. $R_1$ and $R_2$ are particularly preferably identical.

Straight-chain or branched perfluoroalkyl groups having 1 to 12 C atoms conform to the formula $C_mF_{2m+1}$ where m=1, 2, 3, 4, 5, 6, 7, 8, 9, 10, 11 or 12. Preferred perfluoroalkyl groups are straight-chain or branched perfluoroalkyl groups having 1 to 8 C atoms.

The substituent $R_f$ preferably stands for trifluoromethyl, pentafluoroethyl, heptafluoropropyl, straight-chain or branched nonafluorobutyl, straight-chain perfluorohexyl or straight-chain perfluorooctyl. The substituent $R_f$ particularly preferably stands for pentafluoroethyl, heptafluoropropyl, linear or branched nonafluorobutyl. The substituent $R_f$ very particularly preferably stands for pentafluoroethyl or nonafluorobutyl.

Straight-chain or branched alkyl groups having 1 to 4, 1 to 6, 1 to 8 or 1 to 12 C atoms conform to the formula $C_pH_{2p+1}$ where p=1, 2, 3 or 4, or 1, 2, 3, 4, 5 or 6, or 1, 2, 3, 4, 5, 6, 7 or 8, or 1, 2, 3, 4, 5, 6, 7, 8, 9, 10, 11 or 12, for example methyl, ethyl, i-propyl, propyl, butyl, i-butyl or tert-butyl, furthermore also pentyl, 1-, 2- or 3-methylbutyl, 1,1-, 1,2- or 2,2-dimethylpropyl, 1-ethylpropyl or hexyl, heptyl, octyl, furthermore also nonyl, decyl, undecyl or dodecyl.

If an alkyl group is not specified in greater detail, it is a straight-chain alkyl group.

An unsubstituted or substituted arylene is derived from an aryl group having 6 to 12 C atoms, for example from phenyl, naphthyl or anthryl. The unsubstituted or substituted arylene preferably corresponds to unsubstituted or substituted phenylene.

Substituted arylene denotes arylene which is substituted by $C_1$- to $C_6$-alkyl, $C_2$- to $C_6$-alkenyl, F Cl, Br, OH, unfluorinated, partially fluorinated or perfluorinated $C_1$-$C_6$-alkoxy, where the substituents are each selected independently of one another. A preferred substituted arylene is tetrafluorophenylene, tetrachlorophenylene or trifluoromethylphenylene.

The variable n preferably stands for an integer from 1 to 12.

The variable m preferably stands for an integer from 1 to 12.

The variable $m_1$ preferably stands for an integer from 1 to 3, particularly preferably for 2.

The variable $m_2$ preferably stands for an integer from 1 to 3.

$R_1$ and/or $R_2$ preferably stand for H, F or Cl.

In compounds of the formula I, $R_f$ is preferably a straight-chain or branched perfluoroalkyl group having 1 to 8 C atoms.

Accordingly, the invention preferably relates to compounds of the formula I, as described above, where $R_f$ denotes a straight-chain or branched perfluoroalkyl group having 1 to 8 C atoms. $R_f$ is particularly preferably a straight-chain or branched perfluoroalkyl group having 1 to 4 C atoms. $R_f$ is very particularly preferably pentafluoroethyl.

In compounds of the formula I, B is preferably —$(CR_1R_2)_n$—, arylene or substituted arylene, where $R_1$; $R_2$, arylene and substituted arylene have a meaning indicated above.

Accordingly, the invention preferably relates to compounds of the formula I, as described above or described as preferred, where B denotes —$(CR_1R_2)_n$—, arylene or substituted arylene and where $R_1$, $R_2$, arylene and substituted arylene have a meaning indicated above.

In an embodiment of the invention, compounds of the formula I are preferred if A and X have the same meaning. In this embodiment, A and X are preferably H, F or Cl, particularly preferably H or F, very particularly preferably F.

Accordingly, the invention preferably relates to compounds of the formula I, as described above or described as preferred, where A and X are identical. In this embodiment, if A and X are identical, B if preferably —$(CR_1R_2)_n$—, arylene or substituted arylene, as described above. In this embodiment, $R_1$ and $R_2$ are preferably identical and correspond to H, F or Cl, particularly preferably H or F, very particularly preferably H. If A and X are preferably H and B denotes —$(CR_1R_2)_n$—, $R_1$ and $R_2$ are preferably H. If A and X preferably F and B denotes —$(CR_1R_2)_n$—, $R_1$ and $R_2$ are preferably F or H, particularly preferably H. If A and X are preferably H and B denotes arylene, the corresponding arylene is preferably employed in unsubstituted form. If A and X are preferably F and B denotes arylene, the corresponding F-substituted or unsubstituted arylene is preferably employed. If A and X are preferably Cl and B denotes arylene, the corresponding unsubstituted arylene is preferably employed.

In another embodiment of the invention, compounds of the formula I are preferred if A corresponds to a straight-chain or branched alkyl group having 1 to 12 C atoms.

Accordingly, the invention likewise relates to compounds of the formula I, as described above or described as preferred, where A denotes a straight-chain or branched alkyl group having 1 to 12 C atoms. In this embodiment, A and X are not identical.

In this embodiment, if A and X are not identical, A is preferably methyl or ethyl and X, $R_1$, and $R_2$ are preferably, independently of one another, H, F or Cl. In this embodiment, A is particularly preferably methyl and X, $R_1$ and $R_2$ are particularly preferably H, F or Cl, very particularly preferably H or F and very particularly preferably H. In this embodiment, B is preferably —$(CR_1R_2)_n$—, arylene or substituted arylene, as described above. If X is preferably H and B denotes arylene, the corresponding arylene is preferably employed in unsubstituted form. If X is preferably F and B denotes arylene, the corresponding F-substituted or unsubstituted arylene is preferably employed. If X is preferably Cl and B denotes arylene, the corresponding unsubstituted arylene is preferably employed.

In an embodiment of the invention, particular preference is given to compounds of the formula I, as described above, in which B denotes —$(CR_1R_2)_n$—. In particularly preferred compounds of this embodiment, the variable n stands for 1, 2, 4 or 9.

Very particularly preferred compounds of the formula I are allylpentafluoroethylphosphinic acid,
allylnonafluorobutylphosphinic acid,
pentafluoroethyl(but-3-en-1-yl)phosphinic acid,
nonafluorobutyl(but-3-en-1-yl)phosphinic acid,
pentafluoroethyl(undec-10-en-1-yl)phosphinic acid,
nonafluorobutyl(undec-10-en-1-ylphosphinic acid,
pentafluoroethyl-4-styrylphosphinic acid,
nonafluorobutyl-4-styrylphosphinic acid,
pentafluoroethyl(3,4,4-trifluorobut-3-en-1-yl)phosphinic acid
nonafluorobutyl(3,4,4-trifluorobut-3-en-1-yl)phosphinic acid,
nonafluorobutyl(1,2,2-trifluorovinyl)phosphinic acid,
pentafluoroethyl(1,2,2-trifluorovinyl)phosphinic acid.

The present invention likewise relates to processes for the preparation of compounds of the formula I, as described above or described as preferred.

The invention therefore relates to a process for the preparation of compounds of the formula I, as described above or described as preferred, characterised in that a) a compound of the formula II $$(F)_x(R_f)_{4-x}P—B—CX=CX-A \qquad II,$$

where $R_f$, A, B and X have one of the meanings indicated above or indicated as preferred and x denotes 1 or 2, is hydrolysed, giving an intermediate compound of the formula IIIa as intermediate, IIIa

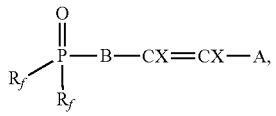

where $R_f$, A, B and X have a meaning indicated in formula II, or b) a compound of the formula II $$(F)_x(R_f)_{4-x}P—B—CX=CX-A \quad \text{II,}$$

where $R_f$, A, B and X have one of the meanings indicated above or indicated as preferred and x denotes 1, 2 or 3, is reacted with a hexaalkyldisiloxane without or in the presence of a catalytic amount of water, where the alkyl groups of the hexaalkyldisiloxane each, independently of one another, denote a straight-chain or branched alkyl group having 1 to 4C atoms, giving an intermediate compound of the formula III,

III

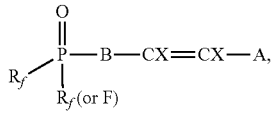

where $R_f$, A, B and X a have a meaning indicated in formula II, which is subsequently hydrolysed.

The compounds of the formula II, as described above, can be prepared, for example, by reacting a phosphorane, selected from the group difluorotris(perfluoroalkyl)phosphorane, trifluorobis(perfluoroalkyl)phosporane or tetrafluoro(perfluoroalkyl)phosphorane, under inert-gas conditions with an alkenylmagnesium bromide (A-CX=CX—B—MgBr) or an alkenylmagnesium chloride (A-CX=CX—B—MgCl) or an alkenyllithium (A-CX=CX—B—Li) or with di(alkenyl)zinc [$(A\text{-}CX=CX—B)_2Zn$] or with alkenylzinc chloride (A-CX=CX—B—ZnCl).

The perfluoroalkyl group, A, X and B in the formulae indicated have a meaning as described above for the formula I.

The choice of the organic metal compound required depends on the reactivity, stability and steric hindrance of the alkenyl group A-CX=CX—B— used, as described above.

Inert-gas conditions in the sense of the invention mean that working is carried out in the presence of an inert gas, for example nitrogen, dried nitrogen, dried argon or argon.

The synthesis of the phosphoranes via electrochemical fluorination is described, for example, in WO 00/21969. Alternatively, for example, a bis(perfluoroalkyl)trifluorophosphorane can be prepared by reaction of tetrafluorobis(perfluoroalkyl)phosphate salts with $SbF_5$ or $SbCl_5$, as described in WO 2005/049628.

Hexaalkyldisiloxanes are in some cases commercially available or can be prepared analogously by known processes. Suitable alkyl groups are preferably identical and are preferably selected from methyl, ethyl, propyl or butyl. Hexamethyldisiloxane is preferably used.

The hydrolysis of the compounds of the formula II, as described above as process variant a), is preferably carried out at a temperature of 0° C. to 100° C. The reaction may be exothermic. The final temperature for complete reaction is preferably 60 to 80° C. The speed of the hydrolysis is dependent on the length of the perfluoroalkyl group $R_f$ and the steric size of the alkenyl group —B—CX=CXA in the phosphorane of the formula II.

The alternative reaction of the compounds of the formula II, as described above, with a hexaalkyldisiloxane, in process variant b) as described above, is preferably carried out without solvent at temperatures of 0° C. to 120° C., particularly preferably at 80° C. to 100° C., if X denotes H and particularly preferably at 0° C. to 60° C. if X denotes F.

Alternatively, the reaction can also be carried out in the presence of a solvent. Suitable solvents are n-hexane, 1,4-dioxane, benzene or toluene.

Both in the case of hydrolysis and also in the case of reaction with a hexa-alkyldisiloxane to give the compounds of the formula I, the corresponding alkenylbis(perfluoroalkyl)phosphine oxides of the formula III or IIIa,

III

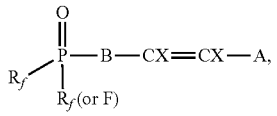

IIIa

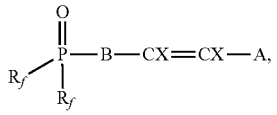

where $R_f$, A, B and X have a meaning indicated above or a meaning preferably indicated, form as intermediate compounds.

Owing to its reactivity, the compound of the formula III formed as intermediate is generally not isolated. However, isolation is possible if it desired to characterise the specific compound of the formula IIIa, IIIa

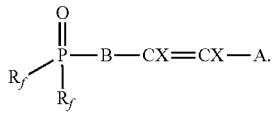

Suitable measures would be extraction and/or distillative separation.

In process variant b), the intermediate compound of the formula III formed can, if this conforms to the formula IIIa, as described above, be isolated and purified before the further hydrolysis is carried out. However, this is likewise not absolutely necessary. Process variant b) can also be carried out as a one-pot variant in which the two reaction steps are carried out successively.

The hydrolysis of the compounds of the formula III or of the formula IIIa, as described above, is preferably carried out at temperatures of 30 to 100° C., particularly preferably at 40° C. to 60° C., with a reaction duration of several hours. The hydrolysis can alternatively preferably be carried out at temperatures of 80° C. to 120° C., preferably at 100° C., with a reaction duration of 1 to 10 hours.

The hydrolysis can alternatively also be carried out in the presence of a solvent. Suitable solvents are acetonitrile, propionitrile, dioxane, dimethoxyethane, dimethyl sulfoxide, dimethylformamide, or alcohols, for example methanol, ethanol or isopropanol, or mixtures of the said solvents.

The invention accordingly furthermore also relates to the compounds of the formula IIIa,

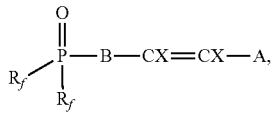

IIIa where $R_f$ denotes a straight-chain or branched perfluoroalkyl group having 1 to 12 C atoms, A denotes H, F, Cl or a straight-chain or branched alkyl group having 1 to 12 C atoms, B denotes $—(CR_1R_2)_n—$, $[—(CR_1R_2)_m—O—(CR_1R_2)_{m1}—]_{m2}$, arylene or substituted arylene, X denotes H, F and/or Cl, n denotes an integer from 0 to 20, m denotes an integer from 1 to 20, $m_1$ denotes an integer from 0 to 8, $m_2$ denotes an integer from 1 to 20 and $R_1$ or $R_2$ each, independently of one another, denote H, F, Cl or a straight-chain or branched alkyl group having 1 to 12 C atoms.

The description of the meanings or of the preferred meanings of $R_f$, A, B and X in compounds of the formula I also applies correspondingly to the intermediate compounds of the formula III or the intermediate compounds of the formula IIIa.

The invention accordingly furthermore likewise relates to a process for the preparation of compounds of the formula IIIa, as described above, characterised in that a compound of the formula II $$(F)_x(R_f)_{4-x}P—B—CX=CX\text{-}A \qquad \text{II,}$$

where $R_f$, A, B and X have one of the meanings indicated above or indicated as preferred and x denotes 1 or 2, is hydrolysed by reaction with water in an organic solvent.

Suitable solvents are, for example, acetonitrile, propionitrile, dioxane, dimethoxyethane, dimethyl sulfoxide, dimethylformamide, or alcohols, for example methanol, ethanol or isopropanol, or mixtures of the said solvents.

The yield of compounds of the formula IIIa is dependent on the solvent used and the amount of water.

The invention furthermore likewise relates to a process for the preparation of compounds of the formula IIIa, as described above, characterised in that a compound of the formula II $$(F)_x(R_f)_{4-x}P—B—CX=CX\text{-}A \qquad \text{II,}$$

where $R_f$, A, B and X have one of the meanings indicated above or indicated as preferred and x denotes 1 or 2, is reacted with alkaline-earth metal oxides, alkaline-earth metal carbonates, zinc oxide, copper(I) oxide, copper(II) oxide, silver oxide, mercury(II) oxide, cadmium oxide or cadmium carbonate.

In principle, all alkaline-earth metal oxides or alkaline-earth metal carbonates can be employed in the process according to the invention. As is known, alkaline-earth metals are magnesium, calcium, strontium and barium. Commercially interesting alkaline-earth metal oxides or alkaline-earth metal carbonates are, for example, calcium oxide (CaO), calcium carbonate ($CaCO_3$), magnesium oxide (MgO) or barium carbonate ($BaCO_3$). The said metal oxides or metal carbonates, as described above, can be used in equimolar amount or up to a two-fold excess.

For the synthesis of the compounds of the formula IIIa, as described above, preference is given to an embodiment of the invention in which alkaline-earth metal oxides or alkaline-earth metal carbonates are employed. The invention therefore relates to a process, as described above, characterised in that alkaline-earth metal oxides or alkaline-earth metal carbonates are used. These are preferably selected from CaO, $CaCO_3$, MgO or $BaCO_3$.

Calcium oxide is very particularly preferably used.

The solids employed in the process according to the invention should preferably be employed in the ground state in order that the largest possible surface area is present for the reaction.

Any type of grinding is possible, for example grinding by means of a ball mill.

Another alternative is the use of metal oxides in the form of fine particles having a diameter of 10 nm to 0.1 mm, which are preferably employed in freshly prepared form in the process according to the invention. The preparation of such highly active metal oxides from corresponding precursor materials is known to the person skilled in the art and can be carried out by methods which are known in the literature. For example, highly active metal oxides of this type can be prepared by sol-gel processes in which a suitable precursor compound, for example a corresponding metal acetate, is hydrolysed in alcohol or an alcohol/water mixture.

In the case of the alkaline-earth metal oxides or alkaline-earth metal carbonates, it is preferred to dry the solids in advance. In general, however, a proportion of at most 10 mol % of water is tolerated in the process according to the invention. In exceptional cases, such as, for example, on use of copper(I) oxide, the proportion of water described even results in an acceleration of the reaction.

The reaction can in principle be carried out at temperatures between 15° C. and 200° C. If lower reaction temperatures are selected, the corresponding reaction time is longer.

The invention therefore also relates to a process, as described above, characterised in that the reaction is carried out at temperatures between 15° C. and 200° C.

The reaction is preferably carried out at room temperature if long reaction times in the order of days are desired.

The reaction is preferably carried out at reaction temperatures of 50° C. to 150° C., particularly preferably at reaction temperatures of 70° C. to 130° C.

The reaction can be carried out in a glass apparatus or in an apparatus made from plastic (such as, for example, Teflon) or steel.

The reaction in the plastic apparatus or in the steel apparatus generally takes longer The reaction is preferably carried out without solvents. However, it is also possible to carry out the reaction in the presence of solvents which are inert to the compounds employed, for example dialkyl ethers containing alkyl groups having 2 to 4 C atoms, for example diethyl ether, diisopropyl ether, dipropyl ether, dibutyl ether.

The metal fluorides formed are virtually insoluble and can easily be separated off, for example, by filtration or decantation.

The reaction conditions in this embodiment are derived from the reaction conditions described in WO 2011/110281, in particular from Examples 1 to 5.

The invention furthermore likewise relates to a process for the preparation of compounds of the formula IIIa, as described above, characterised in that a compound of the formula II $$(F)_x(R_f)_{4-x}P—B—CX=CX\text{-}A \qquad \text{II,}$$

where $R_f$, A, B and X have one of the meanings indicated above or indicated as preferred and x denotes 1 or 2, with non-metal oxides, semimetal oxides or organic compounds containing basic oxygen residues.

In principle, all non-metal oxides, semimetal oxides or organic compounds containing basic oxygen residues can be employed in the process according to the invention for the preparation of the compounds of the formula IIIa. Non-metal oxides are, as is known, oxides of carbon, nitrogen, phosphorus or sulfur, but also selenium, semimetal oxides are oxides of boron, silicon, arsenic or tellurium. Economically interesting non-metal oxofluorides are $COF_2$, $P(O)F_3$, $S(O)F_2$ The said organic oxo compounds, as well as the non-metal or semimetal oxides, as described above, can be used in equimolar amount or large excess.

Non-metal oxides preferably used are $SO_2$, $POCl_3$, $P_4O_{10}$, $CO_2$, $SeO_2$, in particular $SO_2$, $CO_2$ and $SeO_2$.

A semimetal oxide which is preferably used is $SiO_2$.

Organic compounds containing basic oxygen residues which are preferably used are triphenylphoshine oxide ($Ph_3PO$), ethylene carbonate or dimethyl carbonate, in particular ethylene carbonate.

For the synthesis of the compounds of the formula IIIa, as described above, preference is given to an embodiment of the invention in which the non-metal oxides and semimetal oxides are employed, in particular the compounds mentioned as preferred. The invention therefore relates to a process, as described above, characterised in that non-metal oxides and semimetal oxides are used. Particular preference is given to the use of silicon dioxide, selenium dioxide or sulfur dioxide.

The reaction times can be reduced significantly if small amounts of water are added. Water can be added her in a molar proportion of 0.01 to 0.8equivalents. 0.1 to 0.5 equivalents of water are preferably added. Due to the addition of larger amounts of water, preferably 0.5 to 1.0 equivalents of water, some of the product reacts further to give the corresponding phosphinic acids of the formula I and liberated HF forms the corresponding (perfluoroalkyl) fluorophosphates with some of the starting material.

The solids employed in this process should preferably be employed in the ground state in order that the largest possible surface area is present for the reaction. Any type of grinding is possible, for example grinding by means of a ball mill.

The solids do not require any type of drying. In general, the proportion of water described results in an acceleration of the reaction.

The reaction can in principle be carried out at temperatures between 80° C. and 200° C. If low reaction temperatures are selected, the corresponding reaction time is longer. The invention therefore also relates to a process, as described above, characterised in that the reaction is carried out at temperatures between 25° C. and 200° C.

The reaction is preferably carried out at room temperature if long reaction times in the order of days are desired.

The reaction is preferably carried out at reaction temperatures of 50° C. to 180° C., particularly preferably at reaction temperatures of 80° C. to 150° C.

The reaction can be carried out in a glass apparatus or in an apparatus made from plastic (such as, for example, Teflon) or steel.

The reaction in the plastic apparatus or in the steel apparatus generally takes longer The reaction is preferably carried out without solvents. However, it is also possible to carry out the reaction in the presence of solvents which are inert to the compounds employed, for example dialkyl ethers containing alkyl groups having 2 to 4 C atoms, for example diethyl ether, diisopropyl ether, dipropyl ether, methyl butyl ether.

The by-products formed are gaseous and can easily be separated off. Reactions in which solids were used can easily be separated off, for example, by filtration or decantation or condensed off or distilled off in vacuo.

Isolation of the products is not necessary in the case of gaseous reactants. The by-products are discharged continuously on use of cooling above the boiling point of the by-products. The residue is principally product. However, the compounds of the formula IIIa or I can also be separated off by condensation or distillation from solid by-products formed.

The reaction conditions in this embodiment are derived from the reaction conditions described in WO 2014/005668, in particular from Examples 1 to 9.

The invention furthermore likewise relates to a process for the preparation of compounds of the formula IIIa, as described above, characterised in that a compound of the formula II $$(F)_x(R_f)_{4-x}P—B—CX=CX\text{-}A \qquad \text{II,}$$

where $R_f$, A, B and X have one of the meanings indicated above or indicated as preferred and x denotes 1 or 2, is reacted with a hexaalkyldisiloxane without or in the presence of a catalytic amount of water, where the alkyl groups of the hexaalkyldisiloxane each, independently of one another, denote a straight-chain or branched alkyl group having 1 to 4 C atoms.

The compounds of the formula I, as described above, can alternatively be prepared by hydrolysis of the intermediate compounds of the formula III if the intermediate compounds of the formula III are accessible by a route other than via reaction of a compound of the formula II, as described above.

The invention accordingly furthermore likewise relates to a process for the preparation of compounds of the formula I, as described above or preferably described, characterised in that a compound of the formula III is hydrolysed,

III

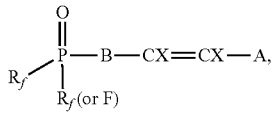

where $R_f$, A, B and X have one of the meanings indicated above or preferred meanings.

The compound of the formula I prepared by the said processes is preferably purified by conventional methods. Suitable purification steps include separating off readily volatile components by distillation or condensation, extraction with an organic solvent or a combination of these methods. Any known separation method can be used or combined for this purpose.

The invention furthermore relates to the use of the compounds of the formula I, as described above or described as preferred, for the preparation of oligomers or polymers.

The term "polymer" generally denotes a molecule having a high relative molecular weight whose structure essentially comprises the multiple repetition of units which are actually or conceptually derived from molecules having a low relative molecular weight (PAC, 1996, 68, 2291). The term "oligomer" generally denotes a molecule having a moderate relative molecular weight whose structure essentially comprises a small number of units which are actually or conceptually derived from molecules having a lower relative molecular weight (PAC, 1996, 68, 2291). In a preferred meaning in accordance with the present invention, a polymer denotes a compound having >1, preferably ≥5 repeating units, and an oligomer denotes a compound having >1 and <10, preferably <5 repeating units. The number of monomer units in a macromolecule is also called degree of polymerisation.

Unless indicated otherwise, the molecular weight indicated is the number average molecular weight $M_n$ or weight average molecular weight $M_W$, which is determined by gel permeation chromatography (GPC) against polystyrene standards in eluting solvents, such as tetrahydrofuran, trichloromethane (TCM, chloroform), chlorobenzene or 1,2,4-trichlorobenzene. The degree of polymerisation (n) denotes the number average degree of polymerisation, given by $n=M_n/M_U$, in which $M_U$ is the molecular weight of the individual repeating unit, as described in J. M. G. Cowie, Polymers: Chemistry & Physics of Modern Materials, Blackie, Glasgow, 1991.

The terms "repeating unit" and "monomer unit" denote the basic repeating unit (constitutional repeating unit—CRU), which is the smallest basic unit whose repetition represents a regular macromolecule, a regular oligomer molecule, a regular block or a regular chain (PAC, 1996, 68, 2291). The term "unit" denotes a structural unit which may itself be a repeating unit or can form a repeating unit together with other units.

The oligomer or polymer, as described above, may, besides the polymerised compounds of the formula I, as described above or described as preferred, also contain alternative polymerised monomer units. In a preferred embodiment of the invention, the polymers are homopolymers. In a homopolymer, the polymer consists of the polymerised compounds of the formula I, as described above, as monomer unit.

The invention accordingly furthermore relates to an oligomer or polymer containing the polymerised compounds of the formula I, as described above or described as preferred, as monomer unit.

The invention accordingly furthermore relates to an oligomer or polymer consisting of polymerised compounds of the formula I, as described above or described as preferred, as monomer unit.

The invention accordingly furthermore relates to a homooligomer or homopolymer consisting of polymerised compounds of the formula I, as described above or described as preferred, as monomer unit.

The oligomers or polymers or homooligomers or homopolymers, as described above, may furthermore be linear or crosslinked.

The choice of crosslinking agents or crosslinking agent here is not limited. Suitable crosslinking agents are known to the person skilled in the art in the area of polymer chemistry and are described below.

The invention furthermore relates to a process for the preparation of oligomers or polymers, as described above, characterised in that compounds of the formula I, as described above or described as preferred, are polymerised, optionally together with further monomers and optionally in the presence of a crosslinking agent.

The invention furthermore relates to a process for the preparation of homooligomers or homopolymers, as described above, characterised in that compounds of the formula I, as described above or described as preferred, are polymerised, optionally in the presence of a crosslinking agent. A homopolymer is preferably prepared.

The type of polymerisation is not limited. The polymerisation can be anionic, cationic or free-radical. Living polymerisation is also suitable. Graft polymerisation onto a support material is also suitable.

In the case of graft polymerisation, the polymerisation in accordance with the invention is carried out with the aid of cerium(IV) ions.

The invention furthermore relates to the process for the preparation of oligomers or polymers, as described above, where the graft polymerisation is carried out with the aid of cerium(IV) ions.

In accordance with the invention, free-radical polymerisation is preferred. The invention furthermore relates to the process for the preparation of oligomers or polymers, as described above, where the polymerisation is carried out by means of free radicals.

The free-radical polymerisation is preferably carried out with exclusion of oxygen.

The free-radical polymerisation can be initiated by a free-radical initiator, for example by AIBN (2,2'-azobis(2-methylpropionitrile)) or V65 (2,2'-azobis-(2,4-dimethylvaleronitrile)), or by a photoinitiator.

The free-radical initiator is employed, for example, in 0.01 to 15% by weight, based on the totality of monomers. The free-radical initiator is preferably employed in 0.1 to 5% by weight.

In the case of a photopolymerisation initiator, the polymerisation process is initiated by irradiation of the initiator/monomer mixture, where energy beams of light, electrons or γ rays can be used for this purpose. The photopolymerisation generally results in a rapidly crosslinked end product.

The irradiation is preferably carried out with UV light.

The choice of photoinitiator is not limited.

Suitable photoinitiators for irradiation with UV light are, for example, 2-hydroxy-2-methyl-1-phenylpropan-1-one, marketed under the trade name Darocur® 1173 from BASF, or 1-hydroxycylohexyl phenyl ketone, marketed, for example, under the trade name Irgacure® 184 by BASF (Ciba).

A photoinitiator is employed, for example, in 0.1 to 5% by weight, based on the totality of monomers. A photoinitiator is preferably employed in 1% by weight.

In the case of graft polymerisation, the polymerisation process is initiated by cerium(IV) ions, where the compound $[NH_4]_2$cerium$[NO_3]_6$ in an aqueous $HNO_3$ solution is preferably used.

In an embodiment of the invention, the monomers of the formula I or a monomer mixture comprising a compound of the formula I, as described above, are polymerised by means of free radicals in the presence of a crosslinking agent.

Suitable crosslinking agents are, for example, hexadiol diacrylate, divinylbenzene, tripropylene glycol diacrylate, butanediol diacrylate, trimethylol propane triacrylate, dipropylene glycol diacrylate or mixtures thereof. The crosslinking agent used is preferably tripropylene glycol diacrylate (TPGDA).

The crosslinking agent(s) is preferably employed in an amount of 3 to 10 mol %, particularly preferably in 5 mol %, based on the totality of monomers.

In a preferred embodiment of the invention, the polymerisation is carried out without crosslinking agents.

The invention accordingly furthermore relates to process for the preparation of oligomers or polymers or homooligomers or homopolymers, as described above, characterised in that the polymerisation is carried out without crosslinking agents.

In a alternative preferred embodiment of the invention, the polymerisation is carried out with crosslinking agents.

In a further preferred embodiment of the invention, in particular for industrial use, as described below, the polymerisation is carried out in, on or at a support material.

The invention accordingly furthermore relates to a process for the preparation of oligomers or polymers or homooligomers or homopolymers, as described above, characterised in that the polymerisation is carried out in, on or at a support material.

The free-radical polymerisation is preferably carried out at temperatures of 0° C. to 80° C. The polymerisation is particularly preferably carried out at room temperature. The polymerisation is particularly preferably carried out at 60° C. to 70° C. if the polymerisation is carried out onto a porous silica support material.

The graft polymerisation is preferably carried out at temperatures of 20° C. to 60° C. The polymerisation is particularly preferably carried out at 40° C.

In the polymers in accordance with the present invention, the total number of monomer units n is preferably ≥50, very preferably ≥100, particularly preferably ≥500, and preferably up to 5000, very preferably up to 50,000, particularly preferably up to 200,000, including any desired combinations of the above-mentioned lower and upper limits for n.

$M_W$ is preferably at least 5,000, preferably at least 28,000, particularly preferably at least 150,000 and preferably up to 3,000,000, particularly preferably up to 110,000,000.

The polymers according to the invention preferably have an average degree of polymerisation of 25 to 400,000, preferably of 351,600. The average degree of polymerisation is determined via the weight average molecular weight $M_W$ and the polydispersity by means of GPC. The poly-dispersity, also known as nonuniformity U, is a measure of the width of the distribution.

The oligomers or polymers containing polymerised compounds of the formula I as monomer unit or consisting of polymerised compounds of the formula I as monomer unit, as described above, are preferably used, for example, as ion exchanger or as Brønsted acid catalyst.

Due to the phosphinic acid acidic protons present, both the compounds of the formula I and also the corresponding polymers and oligomers, as described above, are capable of effecting ion exchange or effecting catalysis.

The invention therefore furthermore relates to the use of the compounds of the formula I, as described above or described as preferred, or the use of the oligomers/polymers, as described above, or also of the composite materials comprising compounds of the formula I or the oligomers/polymers according to the invention, as described below, as ion exchanger or as Brønsted acid catalyst.

An alternative use, besides the use as ion exchanger, is, for example, the use in organic catalysis for chemical reactions.

A further alternative use of the compounds of the formula I according to the invention, as described above or described as preferred, or the use of the oligomers/polymers, as described above, or also composite materials comprising compounds of the formula I or the oligomers/polymers according to the invention is, for example, the use as catalysts for the generation of gasoline components for increasing the octane number or for the adduction of water onto olefins for the generation of simple alcohols.

The suitability of the oligomers/polymers, as described above, as ion exchanger can be determined by determination of the ion exchange capacity IEC. For this purpose, the corresponding compound is, for example, suspended in aqueous sodium hydroxide solution (0.1 M NaOH) and stirred vigorously at room temperature for 24 h. The resultant supernatant basic solution is subsequently titrated with hydrochloric acid (0.1 M). Further details on this determination are explained in Example 26.

The suitability of the polymers, as described above, as ion exchanger can likewise be confirmed by titration of the polymer material with a caustic lye, for example a sodium hydroxide solution.

Due to the ion exchange, salts of the compounds of the formula I, as described above or described as preferred, and ionic polymers/oligomers containing polymerised salts of the compounds of the formula I as monomer units, on a support material or without a support material, as described above or below, are formed.

The compound of the formula I is a strong acid which is particularly suitable for the preparation of salts of the formula IV.

The invention furthermore likewise relates to the salts of the compounds of the formula I, corresponding to the formula IV,

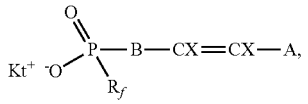

IV or the corresponding ionic polymers/oligomers, as described above, on a support material or without a support material, where the cations of the salts or of the ionic polymers/oligomers $Kt^+$ are an inorganic or organic cation and where $R_f$, A, B and X have one of the meanings indicated above or meanings preferably indicated.

In relation to the choice of the inorganic or organic cation of the salts of the formula IV or of the ionic polymers or oligomers containing polymerised salts of the formula IV as monomeric units on a support material or without a support material, in accordance with the present invention, there are no restrictions per se.

The inorganic cations are preferably the group of cations selected from a cation of an element from group 1, 2, 3, 4, 5, 6, 7, 8, 9, 10, 11 and/or 12 of the Periodic Table.

Salts of this type with inorganic cations, for example $K^+$ or $Na^+$, are suitable, in particular, for the preparation of salts of the formula IV or ionic polymers containing polymerised salts of the formula IV with organic cations or alternative inorganic cations.

The organic cations are preferably organic cations selected from the group comprising ammonium, sulfonium, oxonium, phosphonium, iodonium, tritylium, uronium, thiouronium, guanidinium cations or heterocyclic cations. Examples of organic cations are also polyammonium ions having a degree of charging of 4.

Compounds of the formula IV with organic cations, as described above, then form so-called polymerisable ionic liquids. The uses of ionic liquids are adequately known to the person skilled in the art.

Particularly suitable organic cations are selected from the group tetraalkylammonium, tetraalkylphosphonium, 1,1-dialkylpyrrolidinium, 1-alkyl-1-alkoxyalkylpyrrolidinium or 1,3-dialkylimidazolium, where the alkyl groups or the alkoxy group in the alkoxyalkyl group each have, independently of one another, 1 to 10 C atoms. Very particularly preferably, the alkyl groups have 1 to 6 C atoms and the alkoxy group has 1 to 3 C atoms.

The alkyl groups in tetraalkylammonium or in tetraalkylphosphonium may therefore be identical or different. Preferably, three alkyl groups are identical and one alkyl group is different or two alkyl groups are identical and the other two are different. Preferred tetraalkylammonium cations are, for example, trimethyl(ethyl)ammonium, triethyl(methyl) ammonium, tripropyl(methyl)ammonium, tributyl(methyl) ammonium, tripentyl(methyl)ammonium, trihexyl(methyl) ammonium, triheptyl(methyl)ammonium, trioctyl(methyl)-ammonium, trinonyl(methyl)ammonium, tridecyl(methyl) ammonium, trihexyl(ethyl)ammonium, ethyl(trioctyl) ammonium, propyl(dimethyl)ethylammonium, butyl (dimethyl)ethylammonium, methoxyethyl(dimethyl) ethylammonium, methoxyethyl(diethyl)methylammonium, methoxyethyl(dimethyl)propylammonium, ethoxyethyl(dimethyl)ethylammonium. Particularly preferred quaternary ammonium cations are propyl(dimethyl)ethylammonium, tributyl(methyl)ammonium and/or methoxyethyl(dimethyl) ethylammonium.

Preferred tetraalkylphosphonium cations are, for example, trimethyl(ethyl)phosphonium, triethyl(methyl) phosphonium, tripropyl(methyl)phosphonium, tributyl (methyl)phosphonium, tripentyl(methyl)phosphonium, trihexyl(methyl)phosphonium, triheptyl(methyl) phosphonium, trioctyl(methyl)phosphonium, trinonyl (methyl)phosphonium, tridecyl(methyl)phosphonium, trihexyl(ethyl)phosphonium, ethyl(trioctyl)phosphonium, propyl(dimethyl)ethylphosphonium, butyl(dimethyl)ethylphosphonium, methoxyethyl(dimethyl)ethylphosphonium, methoxyethyl(diethyl)methylphosphonium, methoxyethyl (dimethyl)propyl phosphonium, ethoxyethyl(dimethyl)ethyl phosphonium. Particularly preferred quaternary phosphonium cations are propyl(dimethyl)ethyl phosphonium and/or methoxyethyl(dimethyl)ethylphosphonium.

Preferred 1,1-dialkylpyrrolidinium cations are, for example, 1,1-dimethylpyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octyl-pyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptyl-pyrrolidinium, 1-propyl-1-octylpyrrolidinium, 1-propyl-1-nonylpyrrolidinium, 1-propyl-1-decylpyrrolidinium, 1,1-dibutylpyrrolidinium, 1-butyl-1-methylpyrrolidinium, 1-butyl-1-pentylpyrrolidinium, 1-butyl-1-hexylpyrrolidinium, 1-butyl-1-heptylpyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptylpyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decylpyrrolidinium, 1,1-dinonylpyrrolidinium, 1-nony-1-decylpyrrolidinium or 1,1-didecylpyrrolidinium. Very particularly preference is given to 1-butyl-1-methylpyrrolidinium or 1-propyl-1-methylpyrrolidinium.

Preferred 1-alkyl-1-alkoxyalkylpyrrolidinium cations are, for example, 1-methoxyethyl-1-methylpyrrolidinium, 1-methoxyethyl-1-ethylpyrrolidinium, 1-methoxyethyl-1-propylpyrrolidinium, 1-methoxyethyl-1-butylpyrrolidinium, 1-ethoxyethyl-1-methylpyrrolidinium, 1-ethoxymethyl-1-methylpyrrolidinium. Very particular preference is given to 1-methoxyethyl-1-methylpyrrolidinium.

Preferred 1,3-dialkylimidazolium cations are, for example, 1-ethyl-3-methylimidazolium, 1-methyl-3-propylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethylimidazolium, 1,3-diethylimidazolium, 1,3-dipropypylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium. Particularly preferred cations are 1-ethyl-3-methylimidazolium, 1-butyl-3-methylimidazolium or 1-methyl-3-propylimidazolium.

Particularly preferred organic cations of the compounds of the formula IV for industrial applications of ionic liquids are accordingly 1-butyl-1-methylpyrrolidinium, 1-ethyl-3-methylimidazolium, 1-ethyl-2,3-dimethylimidazolium, 1-butyl-2,3-dimethylimidazolium, 1-(2-methoxyethyl)-3-methylimidazolium, 1-butyl-3-methylimidazolium, tributylmethylammonium, tetra-n-butylammonium, tributylmethylphosphonium, tetraphenylphosphonium, tetrabutylphosphonium, diethylmethylsulfonium, S-ethyl-N,N,N',N'-tetramethylisothiouronium, 1-allyl-3-methylimidazolium, 1-allyl-2,3-dimethylimidazolium, 1-cyanomethyl-3-methylimidazolium, 1-(2-cyanoethyl)-3-methylimidazolium, 1-methyl-3-propinylimidazlium, 1-butyl-4-methylpyridinum, 1,1-dimethylpyrrolidinium.

A particular form of ion exchange is the exchange of protons by cations of the rare earths. There continues to be a demand for alternative compounds for the extraction of cations of the rare earths from solutions, preferably from aqueous solutions, particularly preferably from aqueous acidic solutions.

Particularly preferred inorganic cations of the compounds of the formula IV or of the ionic polymers/oligomers containing polymerised compounds of the formula IV or of the composite materials comprising compounds of the formula IV or ionic polymers/oligomers containing polymerised compounds of the formula IV are the cations of the rare earths.

In a preferred embodiment of the invention, cations of the rare earths are selected from the group Sc, Y, Lu, La, Ce, Pr, Nd, Pm, Sm, Eu, Gd, Tb, Dy, Ho, Er, Tm and Yb.

As is known, rare-earth metal cations can have a valency of 2, 3 or 4. The valency of the corresponding cation is preferably 3 (z=3).

In a particularly preferred embodiment of the invention, cations of the rare earths from the group Y, La, Ce, Pr, Nd, Sm, Eu, Gd and Tm are extracted.

The invention therefore furthermore relates to the use of the compounds of the formula I described above or of the corresponding polymers/oligomers containing polymerised compounds of the formula I on a support material or without a support material for the extraction of cations of the rare earths from solutions, preferably from aqueous solutions, particularly preferably from aqueous acidic solutions.

The source of the corresponding solution is not restricted. It may be a corresponding solution which forms during the work-up of commercially available rare-earth minerals, for example during the work-up of bastnesite, monazite or xenotime. However, it may also be a solution which forms as intermediate during the processing of rare-earth metals or rare-earth metal solutions or a solution from waste water or a solution which forms during the recycling of industrial equipment.

The solution can contain one or more rare-earth metal cation(s).

The pH of these solutions is preferably pH 0 to 7.

The proportion of the corresponding cations of the rare-earth metals in the solution is preferably ≤10 per cent by weight.

The aqueous acidic solutions contain, for example, chloride anions, sulfate anions, nitrite anions or nitrate anions or a mixture of the said anions. The aqueous solution preferably contains chloride anions or a mixture of chloride and nitrate anions.

The invention accordingly furthermore also relates to a process for the extraction of cations of the rare earths from solutions, preferably aqueous solutions, particularly preferably from aqueous acidic solutions, using a compound of the formula I, as described above, or a polymer/oligomer containing polymerised compounds of the formula I, as described above, or a composite material comprising a polymer/oligomer comprising or consisting of polymerised monomer units of the formula I, as described below.

The extraction according to the invention is preferably carried out by a) providing the solution containing the cations of the rare earths, b) mixing the aqueous solution from a) with b1) at least one compound of the formula I, as described above, b2) a polymer or oligomer containing polymerised compounds of the formula I, as described above, or b3) a composite material comprising a support material and either a compound of the formula I or a polymer or oligomer containing polymerised compounds of the formula I, as described below, so that at least some of the acidic protons of the phosphinic acid function are replaced by the cations of the rare earths in order to extract these cations from the solution, where corresponding salts or ionic polymers/oligomers form, c) separating off the salts of the compounds of the formula I or of the ionic polymers or oligomers containing polymerised salts of the compounds of the formula I or of the composite material from the aqueous solution and optionally d) regenerating to form compounds of the formula I or to form polymers or oligomers containing polymerised compounds of the formula I or of the composite material.

The extraction can be carried out discontinuously in a batch process or continuously in through-flow, for example as co-current or countercurrent process.

The regeneration of the compounds of the formula I, as described above, of the polymers or oligomers containing polymerised compounds of the formula I, as described above, or of the composite material comprising a compound of the formula I or a polymer or oligomer containing polymerised compounds of the formula I, as described below, is carried out, for example, by exchange of the cation of the rare-earth metal by an acid. Suitable acids for the regeneration are hydrochloric acid, sulfuric acid or nitric acid or a mixture of the said acids.

If a liquid-phase extraction is carried out, firstly a phase separation is carried out and then the cations of the rare earths are separated off, where rinsing is carried out, for example, with an aqueous acid. Suitable acids are listed above. The further work-up of the aqueous solution containing the cations of the rare earths is then dependent on the corresponding application.

In a preferred embodiment of the invention, a polymer containing polymerised compounds of the formula I, as described above or described as preferred, is employed as extraction medium.

In a alternative preferred embodiment of the invention, a polymer containing polymerised compounds of the formula I, as described above or described as preferred, combined with a support material is employed. In this embodiment of a composite material, the separation from the aqueous solution is the simplest.

The polymerisation can take place within the support material or merely at the surface of the support material. The polymer formed containing the polymerised monomer units of the formula I or consisting of the polymerised monomer units of the formula I can covalently bond to the support material. However, the invention also encompasses support materials comprising oligomers/polymers containing or consisting of polymerised monomer units of the formula I which are merely adsorbed at the surface or in the pores or in which the polymerisation takes place in the pores.

The invention furthermore relates to a composite material comprising a support material and at least one compound of the formula I, as described above, or a support material and a polymer or oligomer containing polymerised compounds of the formula I, as described above or described as an alternative or preferred, or a corresponding salt or polymerised salts of the formula IV after successful ion exchange.

The composite material preferably comprises a support material and a polymer containing polymerised compounds of the formula I, as described above or described as preferred.

The composite material preferably comprises a support material and a polymer consisting of polymerised compounds of the formula I, as described above or described as preferred.

The composite material may comprise or contain, essentially consist of or consist of the said requisite or optional constituents. All compounds or components which can be used in the composite material are either known and commercially available, can be synthesised by known processes or are as described above or below.

A suitable support material is any form of a matrix, for example a porous material, a film, a fibre or a hollow fibre. The porous material can be a particle or a monolithic shaped body.

Suitable as support material are inorganic materials, organic materials or a composite material comprising inorganic and organic materials.

Suitable support materials are, for example, polymer support materials, which may likewise be porous.

Suitable support materials are polysulfones, polyether sulfones, polyphenyl sulfones, polyimides, polyamides, polyvinylidene fluoride (PVDF), polyacrylonitriles, polyacrylamides, polyacrylates, polyaniline, polyetherimides, polyvinyl ethers, polystyrenes or cellulose acetate.

A preferred polyvinyl ether is a hydrophilically crosslinked polyvinyl ether.

A particularly preferred polymer as support material is a hydrophilic crosslinked polymer based on a copolymer at least of a) at least one hydrophilically substituted alkyl vinyl ether of the formula 1

1

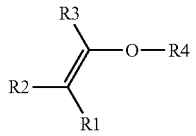

where R1, R2, R3, independently of one another, can be H or C1 to C6 alkyl, preferably H or —$CH_3$ and R4 is a radical which carries at least one hydroxyl group and b) at least one crosslinking agent conforming to formula 2 and/or 3 and/or 4, with

2

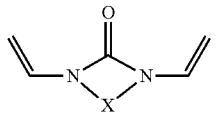

where X in the formula 2 is a divalent alkyl radical having 2 to 5 C atoms, preferably 2 or 3 C atoms, in which one or more non-adjacent methylene groups which are not located in the direct vicinity of N may be replaced by O, C═O, S, S═O, $SO_2$, NH, NOH or N and one or more H atoms of the methylene groups may be substituted, independently of one another, by hydroxyl groups, C1-C6-alkyl, halogen, $NH_2$, C5-C10-aryl, NH—(C1-C8)-alkyl, N—(C1-C8)-$alkyl_2$, C1-C6-alkoxy or C1-C6-alkyl-OH, and

3

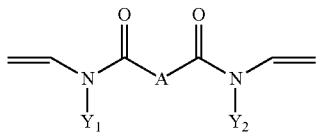

-continued

4

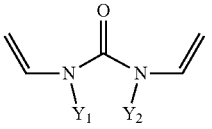

where $Y_1$ and $Y_2$ in formula 3 and 4 are, independently of one another, C1 to C10 alkyl or cycloalkyl, where one or more non-adjacent methylene groups or methylene groups which are not located in the direct vicinity of N may be replaced by O, C═O, S, S═O, $SO_2$, NH, NOH or N and one or more H of the methylene groups may be substituted, independently of one another, by hydroxyl groups, C1-C6-alkyl, halogen, $NH_2$, C5-C10-aryl, NH(C1-C8)alkyl, N(C1-C8)$alkyl_2$, C1-C6-alkoxy or C1-C6-alkyl-OH, or are C6 to C18 aryl, where one or more H in the aryl system may be substituted, independently of one another, by hydroxyl groups, C1-C6-alkyl, halogen, $NH_2$, NH(C1-C8)alkyl, N(C1-C8)$alkyl_2$, C1-C6-alkoxy or C1-C6-alkyl-OH and A in this formula 3 is a divalent alkyl radical having 2 to 5 C atoms, preferably 2 or 3 C atoms, in which one or more non-adjacent methylene groups or methylene groups which are not located in the direct vicinity of N may be replaced by O, C═O, S, S═O, $SO_2$, NH, NOH or N and one or more H of the methylene groups may be substituted, independently of one another, by hydroxyl groups, C1-C6-alkyl, halogen, $NH_2$, C5-C10-aryl, NH(C1-C8)alkyl, N(C1-C8)$alkyl_2$, C1-C6-alkoxy or C1-C6-alkyl-OH, as described in WO 2007/014591.

In a particularly preferred embodiment, the hydrophilically substituted alkyl vinyl ether employed is 1,2-ethanediol monovinyl ether, 1,3-propanediol monovinyl ether, 1,4-butanediol monovinyl ether, 1,5-pentanediol monovinyl ether, 1,6-hexanediol monovinyl ether or diethylene glycol monovinyl ether and the cycloaliphatic vinyl ether employed is cyclohexanedimethanol monovinyl ether.

in a further preferred embodiment, the crosslinking agent employed is divinylethyleneurea (1,3-divinylimidazolin-2-one) or divinylpropyleneurea (1,3-divinyltetrahydropyrimidin-2-one).

In another preferred embodiment, the polymer is porous having pore sizes between 2 and 200 nm.

In another embodiment, the polymer is in the form of particles having a diameter between 3 and 300 μm.

The oligomers/polymers according to the invention can preferably be applied to this polymer material by graft polymerisation, for example by graft polymerisation with cerium(IV)catalysis, as described in Example 29.

Further preferred embodiments of this polymer material as support material and the preparation of this polymer material are described in WO 2007/014591, in particular in Example 1.

Suitable natural support materials are carbohydrate polymers, such as, for example, agarose, cellulose, dextran and chitosan (A. Jungbauer, G. Carta, in: Protein Chromatography, Process Development and Scale-Up; WILEY-VCH Verlag, Weinheim (Germany) 2010).

Suitable inorganic support materials are metal oxides, for example $SiO_2$, including silicates and silica gel, $TiO_2$, $ZrO_2$, $Al_2O_3$, ZnO or mixtures thereof, where the inorganic surfaces must have corresponding free edge groups which allow the binding of the monomer unit of the formula I. Corresponding free edge groups are, for example, the OH group or the SH group. In Example 30, for example, the graft polymerisation is carried out on a mercapto-silica gel.

The term inorganic support materials also encompasses ceramic support materials, in which, for example, a mixture of inorganic metal oxides is used, where the mixture also encompasses a sequence of different layers of metal oxides on a metal oxide as substrate.

Suitable inorganic support materials are likewise support materials based on activated carbon.

Suitable support materials are likewise porous glasses having pore diameters of about 50 to 300 microns, which are optionally functionalised by a polymer material, as described above, and which carry reactive groups on which or with which the polymerisation with the monomer units of the formula I according to the invention can take place. Porous glasses of this type are of called "controlled pore glass" (CPG).

The support materials, preferably the porous support materials, can be in particulate or monolithic form.

Monolithic support materials have a porous body in which channels are present which arise through the connection of cavities from one end to the other end of the inorganic support material. The cavities contain a macropore and a mesopore, which forms on the inside surface of the macropore. In general, the mesopores have a pore size of 6 to 100 nm. Further details on monolithic support materials are described, for example, in US 2011/0094955 in paragraphs [0019] to [0029].

Preferred suitable support materials are porous materials in the pores of which the ion exchange or extraction takes place, preferably particulate materials.

Particularly preferred support materials are particulate.

Even without further comments, in will be assumed that a person skilled in the art is able to utilise the above description in the broadest scope. The preferred embodiments and examples should therefore merely be regarded as descriptive disclosure which is absolutely not limiting in any way.

The following examples demonstrate syntheses of compounds of the formula I and use thereof for polymerisation processes, examples of the preparation of polymers and composite materials and examples of ion exchangers and examples of the use as extraction medium.

Apparatuses and Materials

Gaseous or readily volatile substances are handled in grease-free glass vacuum lines. Moisture-sensitive solids are stored and handled in a dry box (Jacomex with the P(SYS)-II-P inert-gas purification module, argon atmosphere; $H_2O$ and $O_2$ range <0.5 ppm). Organic solvents are purified and dried in accordance with the current standard literature, for example as described in Wilfred L. F. Armarego, Christina L. L. Chai, Purification of Laboratory Chemicals, 5th ed.; Butterworth-Heinemann, Elsevier Science, 2003.

NMR spectroscopy: NMR samples are measured at 25° C. either in a 5 mm ($Ø_O$) glass NMR tube or in a 3.7 mm ($Ø_o$) FEP inliner. In the case of measurements in FEP, the inliner is introduced into a 5 mm ($Ø_o$) precision thin-glass NMR tube (Wilmad 537). The lock substance, $CD_3CN$, is thus located between glass and FEP inliner in the glass NMR tube and is characterised below using film measurement or solvent film. The measurements are carried out in a 400 MHz Bruker Avance III spectrometer with a 9.3980 T cryomagnet and a 5 mm BBFO sample head. $^1H$ NMR spectra are measured in the $^1H/^{19}F$ channel at 400.17 MHz. $^{13}C$, $^{19}F$ and $^{31}P$ NMR spectra are measured in the broad-band channel at 100.62, 376.54 and 161.99 MHz. The $^1H$ NMR chemical shifts are relative to tetramethylsilane (TMS) and arise for the solvents $D_2O$ (4.81 ppm), $CDCl_3$ (7.24 ppm) and $CD_3CN$ (1.96 ppm). The $^{13}C$ NMR chemical shifts are likewise relative to TMS and arise for the solvents $CDCl_3$ (77.2 ppm) and $CD_3CN$ (118.7 ppm). The $^{19}F$ NMR chemical shifts are relative to $CFCl_3$ and arise for the internal standards $C_6F_6$ (−162.9 ppm) or $C_6H_5CF_3$ (−63.9 ppm). The $^{31}P$ NMR chemical shifts are relative to $H_3PO_4$ (85%).

The $^{19}F$ NMR spectra of the asymmetrical alkenebis (pentafluoroethyl)phosphinic acids are higher order spectra (AA'BB'). The analysis therefore does not allow direct assignment of the resonance frequencies, which are determined directly as the centre of the AA' or BB' part, or of the coupling constants J and J' or $J_A$ and $J_B$. The line assignment made is checked by calculation of a sample spectrum with the aid of the gNMR program [Version 5.0.6.0; P. H. M. Budzelaar, IvorySoft], taking into account the experimentally determined values from the $^{31}P$ NMR spectra, in order in this way to avoid possible misassignments by precise frequency and intensity comparison with the experiment. The chemical shifts were determined by iterative approximations of the parameters.

Fluorescence Spectroscopy

Fluorescence spectroscopic measurements are carried out using a HITACHI F-2700 fluorescence spectrophotometer. The band pass for excitation the emission is 5 nm.

GPC Analysis

Working Conditions:

Apparatus: Hitachi Elite LaChrom

Eluent: DMF Art. 1.03053 batch K44604953

Sample solvent: ID2013-10-31_KB01

Flow rate: 1.0 ml/min

Pressure: 72 bar

Injection: 100 μL

Separating column: 1×PSS GRAM 100A 8×300 mm SN 3090514+2×PSS GRAM 3000A 8×300 mm SN 3082811+3082814

Column temperature: 40° C.

Detector: RI Hitachi L-2490 cell temp. 40° C., polarity+

Evaluation method: PSS WINGPC Unity

EZChrom method: PMMA.met

EZChrom sequence: POLOXAMER.seq

WINGPC method: POLOXAMER.met

Internal standard: 200 μl of ethylene glycol Art. 109621 batch K38533121 ad 200 ml of eluent=ID2013-10-31_KB01

Sample Preparation:

20-25 mg of the sample are dissolved in 10 ml of sample solvent in a thermoshaker, cooled to room temperature and injected twice each. Before and after the sample injections, sample solvent was injected twice in each case.

Performance of the Analyses:

The standard and sample solutions were each injected twice. Sample solvent was in each case injected twice before, between and after the standard and sample injections.

PMMA Standard Solution:

As calibration solutions, 20-25 mg of PSS PMMA calibration standards Mp 410 mmg14064, Mp 1.020 mmg19113, Mp 1.960 mmg23084, Mp 4.250 mmg24042, Mp 14.300 mmg20124, Mp 23.500 mmg15087, Mp 67.000 mmg2096, Mp 128.000 mmbs15, Mp 263.000 mml19095, Mp 579.000 mm6086, Mp 898.000 mm1086 and Mp 2.740.000 mm7086 were weighed out accurately into a 20 ml volumetric flask, dissolved with sample solvent in the thermomixer and made up to the calibration mark with sample solvent, analysed analogously and a calibration curve was drawn up with polynome 3 as fit.

Evaluation:

Any elution time shifts are corrected via the internal standard.

EXAMPLE 1

Synthesis of allylfluorotris(pentafluoroethyl)phosphorane by Reaction of difluorotris(pentafluoroethyl)phosphorane and allylmagnesium bromide

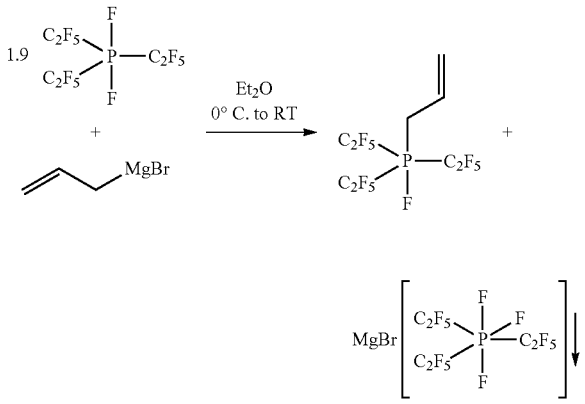

Difluorotris(pentafluoroethyl)phosphorane, $(C_2F_5)_3PF_2$ (82.8 g, 194 mmol), is initially introduced in a 500 ml round-bottomed flask, cooled (0° C.) and emulsified in diethyl ether (100 ml). Allylmagnesium bromide, $CH_2{=}CHCH_2{-}MgBr$ (100 ml of a 1 mol/l solution in diethyl ether; 100 mmol), is added to this emulsion over the course of one hour. A white solid precipitates out, and the reaction mother liquor becomes a yellow colour. The suspension is stirred at 0° C. for 1 hour and at room temperature for 1 hour. The reaction suspension is subsequently filtered, and the solid is washed twice with diethyl ether (25 ml each time). The ether phases are combined and ether and excess $(C_2F_5)_3PF_2$ are condensed off at 0° C. in vacuo ($10^{-1}$ mbar). The yellow liquid remaining consists principally of product, $(C_2F_5)_3PF{-}(CH_2CH{=}CH_2)$, and small amounts of $(C_2F_5)_3PF_2$ and $(C_2F_5)_3P{=}O$. Pure allylfluorotris(pentafluoroethyl)phosphorane, $(C_2F_5)_3PF(CH_2CH{=}CH_2)$ (37.1 g, 83 mmol), can be isolated as a clear and colourless liquid with a yield of 83% by condensation at 30° C. in vacuo ($10^{-3}$ mbar). The isolated product is characterised by means of $^1H$, $^{19}F$ and $^{31}P$ NMR spectra.

NMR (lock substance: $CD_3CN$ film; δ in ppm):

$^1H$ NMR: 3.56 m (2H), 5.32 m (2H), 5.71 m (1H)

$^{19}F$ NMR: −7.3* d, $^1J_{F,P}$=827 Hz (1F), −81.9* m (9F), −122.0* d, $^2J_{F,P}$=80 Hz (6F)

$^{31}P$ NMR: −42.0 d, sep, t, d, $^1J_{P,F}$=822 Hz, $^2J_{P,F}$=78 Hz, $^2J_{P,H}$=14 Hz, $^3J_{P,H}$=5 Hz (1P)

* signals broadened

EXAMPLE 2

Synthesis of allylpentafluoroethylphosphinic acid by Hydrolysis of allylfluorotris(pentafluoroethyl)phosphorane in Water

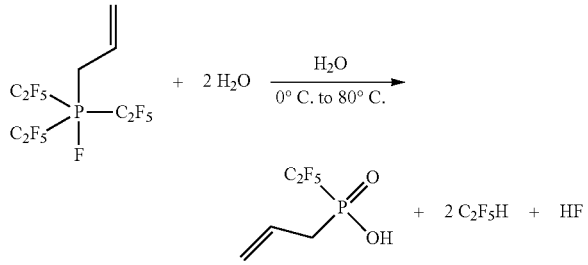

Clear and colourless allylfluorotris(pentafluoroethyl) phosphorane, $(C_2F_5)_3PF(CH_2CH{=}CH_2)$ (33.7 g, 75.2 mmol), is initially introduced in a 100 ml PFA round-bottomed flask, cooled (0° C.), and water (10 ml, ~555 mmol) is slowly added. The reaction is very exothermic and is cooled if necessary using ice (0° C.). The emulsion is stirred at 0° C. to 18° C. for 1 hour, at 35° C. for 1.5 hours, at 50° C. for 1.5 hours and finally at 80° C. for 3 hours. Evolution of gas can be observed constantly. Excess water is subsequently condensed off at 50° C. to 65° C. in vacuo ($10^{-3}$ mbar). The crude product remaining is transferred quantitatively into a 100 ml glass flask and condensed at 100° C. in vacuo ($10^{-3}$ mbar). Allylpentafluoroethylphosphinic acid, $(C_2F_5)(CH_2CH{=}CH_2)P(O)OH$ (14.2 g, 63.5 mmol), can be isolated as a clear and colourless liquid with a yield of 84%. The isolated product is characterised by means of $^1H$, $^{19}F$ and $^{31}P$ NMR spectra.

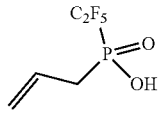

NMR (lock substance: $CD_3CN$ film; δ in ppm)

$^1H$ NMR: 2.24 m (2H), 4.74 m (2H), 5.14 m (1H).

$^{19}F$ NMR: −81.9 m (3F), −128.4 d, $^2J_{F,P}$=73 Hz (2F).

$^{31}P$ NMR: 25.4 t, t, d $^2J_{P,F}$=83 Hz, $^2J_{P,H}$=18 Hz, $^3J_{P,H}$=5 Hz (1P).

EXAMPLE 3

Synthesis of allylbis(pentafluoroethyl)phosphine oxide by Hydrolysis of allylfluorotris(pentafluoroethyl)phosphorane in Water

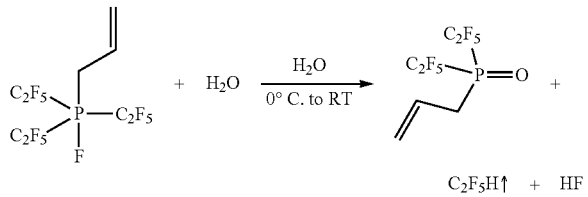

Clear and colourless allylfluorotris(pentafluoroethyl) phosphorane, $(C_2F_5)_3PF(CH_2CH{=}CH_2)$ (11.45 g, 25.5 mmol), is initially introduced in a 23 mm (internal diameter) FEP reactor, cooled (0° C.), and water (1.7 ml, 94 mmol) is added. Two phases form and evolution of gas can be observed. The reaction emulsion is stirred at 0° C. for 1.5 hours and at room temperature for 30 minutes. A conversion of 79% to allylbis(pentafluoroethyl)phoshine oxide, $(C_2F_5)_2P(O)(CH_2CH{=}CH_2)$, can be detected. Secondary compounds are $[H(H_2O)_n][(C_2F_5)_3PF_3]$ (21%) and traces of bis(pentafluoroethyl)phosphinic acid, $(C_2F_5)_2P(O)OH$. The compounds can easily be separated from one another using methods which are known to the person skilled in the art. The mixture can be used without further purification for the further hydrolysis (Example 2). The product is characterised by means of $^1H$, $^{19}F$ and $^{31}P$ NMR spectra.

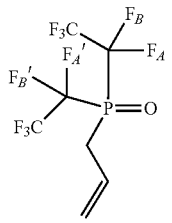

NMR (lock substance: $CD_3CN$ film; δ in ppm)

$^1H$ NMR: 3.40 m (2H), 5.56 m (2H), 5.80 m (1H).

$^{19}F$ NMR: −81.9 m (6F), −122.1 d, m $^2J_{FA,P}$=79 Hz, $^2J_{FB,P}$=71 Hz, $J_{FA,FB}$=341 Hz (2$F_A$), −124.1 d, m, $^2J_{FA',P}$=79 Hz, $^2J_{FB',P}$=71 Hz, $J_{FA',FB'}$=310 Hz (2$F_B$).

$^{31}P$ NMR: 36.4 t, t $^2J_{P,FA}$=$^2J_{P,FA'}$=79 Hz, $^2J_{P,FB}$=$^2J_{P,FB'}$=71 Hz (1P).

EXAMPLE 4

Synthesis of but-3-en-1-ylmagnesium bromide

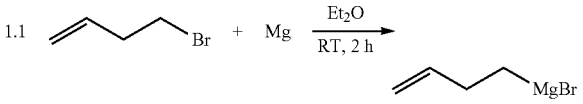

Magnesium turnings (15.81 g, 650 mmol) in diethyl ether (300 ml) are initially introduced in a 500 ml glass round-bottomed flask, and 4-bromo-1-butene (96.20 g, 713 mmol) is added over the course of 2 hours at room temperature. The brown suspension is stirred at room temperature for a further 30 minutes and subsequently filtered. But-3-en-1-ylmagnesium bromide (91%, ~592 mmol) in diethyl ether can be obtained as a brown solution. The only by-product is 1,7-octadiene (9%). This solution is used without further purification. The product is characterised by means of $^1H$ and $^{13}C$ NMR spectra.

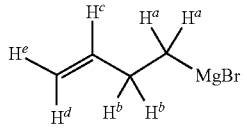

NMR (lock substance: $CD_3CN$ film; δ in ppm)

$^1H$ NMR: −0.57 t $^3J_{H,H}$=8 Hz (2$H^a$), 2.15 t, d, d, d $^3J_{H,H}$=8 Hz, $^3J_{H,H}$=7 Hz, $^4J_{H,H}$=1.5 Hz, $^4J_{H,H}$=1.1 Hz (2$H^b$), 4.52 d, d, t $^3J_{H,H}$=10 Hz, $^2J_{H,H}$=3 Hz, $^4J_{H,H}$=1.1 Hz (1$H^e$), 4.72 d, d, t $^3J_{H,H}$=17 Hz, $^2J_{H,H}$=3 Hz, $^4J_{H,H}$=1.5 Hz (1$H^d$), 5.85 d, d, t $^3J_{H,H}$=17 Hz, $^3J_{H,H}$=10 Hz, $^3J_{H,H}$=7 Hz (1$H^c$)

$^{13}C$ NMR: 7.5 t, m $^1J_{C,H}$=108 Hz, (1$C^a$), 34.1 t, d, d, d $^1J_{C,H}$=123 Hz, $^2J_{C,H}$=5 Hz, $^3J_{C,H}$=5 Hz , $^3J_{C,H}$=5 Hz (1$C^b$), 108.7 d, d, t $^1J_{C,H}$=155 Hz, $^1J_{C,H}$=152 Hz, $^3J_{C,H}$=6 Hz (1$C^d$), 148.3 d, t, m $^1J_{C,H}$=148 Hz, $^2J_{C,H}$=6 Hz (1$C^c$).

EXAMPLE 5

Synthesis of di(but-3-en-1-yl)zinc by Reaction of but-3-en-1-ylmagnesium bromide and Zinc Chloride

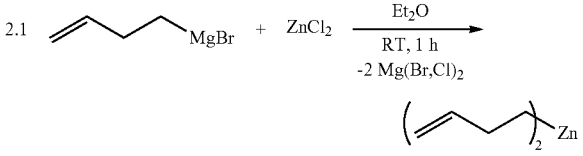

Zinc chloride (37.14 g, 272 mmol) is suspended in diethyl ether (500 ml) in a 100 ml glass round-bottomed flask, and the but-3-en-1-ylmagnesium bromide solution (592 mmol in diethyl ether (300 ml)) described in Example 4 is added over the course of 4 hours. A bulky pale-grey precipitate precipitates out. The suspension is stirred at room temperature for 12 h and then filtered. The grey residue is washed with diethyl ether (60 ml). The yellow filtrate and the wash solution are combined, and the majority of the ether is condensed off at 0° C. in vacuo ($10^{-3}$ mbar). The product is condensed out of the suspension at 30° C. to 40° C. in vacuo ($10^{-3}$ mbar) into a cooled (−196° C.) trap. Residues of diethyl ether and 1,7-octadiene can be removed in a further condensation at −20° C. to −15° C. in vacuo ($10^{-3}$ mbar). Further purification can be achieved by re-condensation of the product at 40° C. in vacuo ($10^{-3}$ mbar). Di(but-3-en-1-yl)zinc (40.59 g, 231 mmol) can be isolated as a clear and colourless liquid with a yield of 85% and a purity of 99%. The isolated product is characterised by means of $^1H$ and $^{13}C$ NMR spectra.

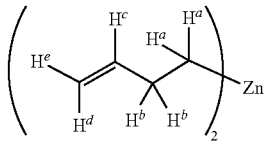

NMR (lock substance: $CD_3CN$ film; δ in ppm)

$^1H$ NMR: 0.40 t $^3J_{H,H}$=8 Hz (4$H^a$), 2.24 t, d, d, d $^3J_{H,H}$=8 Hz, $^3J_{H,H}$=6 Hz, $^4J_{H,H}$=1.7 Hz, $^4J_{H,H}$=1.2 Hz (4$H^b$), 4.84 d, d, t $^3J_{H,H}$=10 Hz, $^2J_{H,H}$=1.8 Hz, $^4J_{H,H}$=1.2 Hz (2$H^e$), 4.94 d, d, t $^3J_{H,H}$=17 Hz, $^2J_{H,H}$=1.8 Hz, $^4J_{H,H}$=1.7 Hz (2$H^d$), 5.92 d, d, t $^3J_{H,H}$=17 Hz, $^3J_{H,H}$=10 Hz, $^3J_{H,H}$=6 Hz (2$H^c$).

$^{13}C$ NMR: 15.9 t, t, d, t $^1J_{C,H}$=121.3 Hz, $^2J_{C,H}$=4.1 Hz, $^2J_{C,H}$=4.0 Hz, $^3J_{C,H}$=1.0 Hz (2$C^a$), 31.3 t, m $^1J_{C,H}$=121.3 Hz (2$C^b$), 113.1 d, d, t, m $^1J_{C,H}$=157.5 Hz, $^1J_{C,H}$=152.3 Hz, $^3J_{C,H}$=6.1 Hz (2$C^d$), 145.0 d, t, d, d, m $^1J_{C,H}$=121.3 Hz, $^2J_{C,H}$=6.2 Hz, $^2J_{C,H}$=6.2 Hz, $^2J_{C,H}$=5.8 Hz (2$C^c$).

EXAMPLE 6

Synthesis of bis(pentafluoroethyl)trifluorophosphorane

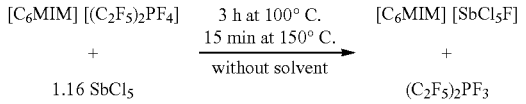

Pale-yellow hexylmethylimidazolium bis(pentafluoroethyl)tetrafluorophosphate, $[C_6MIM][(C_2F_5)_2PF_4]$ (203.0 g, 396 mmol), is initially introduced in a 500 ml glass round-bottomed flask, warmed (100° C.), and freshly distilled yellow $SbCl_5$ (137.7 g; 460 mmol) is added dropwise over the course of 2.5 h. Bis(pentafluoroethyl)trifluorophosphorane, $(C_2F_5)_2PF_3$, (bp 46° C.), formed is condensed directly into a cooled (−78° C.) 300 ml Young U-trap. After a further 30 min at 100° C. and 15 min at 150° C., bis(pentafluoroethyl)trifluorophosphorane, $(C_2F_5)_2PF_3$ (122.1 g; 375 mmol), can be isolated in the trap as a pale-yellow liquid in a yield of 95% (purity 98%). The phosphorane can be used without further purification for subsequent experiments. The isolated product is characterised by means of $^{19}F$ and $^{31}P$ NMR spectra.

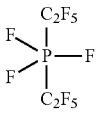

NMR (lock substance: $CD_3CN$ film; δ in ppm)

$^{19}F$ NMR: −55.2 d, qui, sep $^1J_{F,P}$=1145 Hz, $^3J_{F,F}$=11 Hz, $^4J_{F,F}$=7 Hz (3F), −84.1 q, d $^4J_{F,F}$=7 Hz, $^3J_{F,P}$=2 Hz (6F), −119.8 d, q $^2J_{F,P}$=127 Hz, $^3J_{F,F}$=11 Hz (4F)

$^{31}P$ NMR: −40.1 q, qui, sep $^1J_{P,F}$=1145 Hz, $^2J_{P,F}$=127 Hz, $^3J_{P,F}$=2.0 Hz (1P).

EXAMPLE 7

Synthesis of bis(pentafluoroethyl)(but-3-en-1-yl) difluorophosphorane by Reaction of bis(pentafluoroethyl)trifluorophosphorane and di(but-3-en-1-yl) zinc

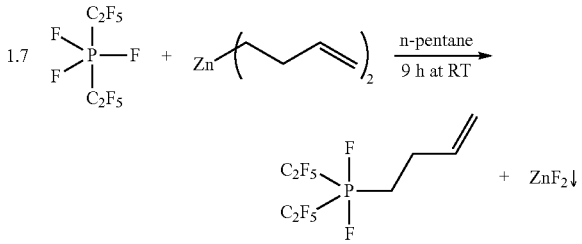

Di(but-3-en-1-yl)zinc (24.27 g, 138 mmol) is dissolved in n-pentane (350 ml) in a 1000 ml glass round-bottomed flask, and bis(pentafluoroethyl)trifluorophosphorane, $(C_2F_5)_2PF_3$ (76.4 g, 234 mmol), is added over the course of 7.5 hours at room temperature. A white solid precipitates out. The suspension is stirred at room temperature for 1.5 hours, and n-pentane is subsequently condensed off at −40° C. to −25° C. in vacuo ($10^{-3}$ mbar). The product which remains is condensed at room temperature in vacuo ($10^{-3}$ mbar). Bis(pentafluoroethyl)(but-3-en-1-yl)difluorophosphorane, $(C_2F_5)_2PF_2$—$(CH_2CH_2CH{=}CH_2)$ (82.08 g, 227 mmol), can be isolated as a clear and colourless liquid with a yield of 97% and a purity of 91%. Bis(pentafluoroethyl)-difluorocyclopropylmethylphosphorane, $(C_2F_5)_2PF_2(CH_2\text{-}c\text{-}C_3H_5)$ (6%) and di(but-3-en-1-yl)zinc (3%) are detected as by-products. This mixture is used without further purification. The impurities can be separated using methods which are known to the person skilled in the art. The product is characterised by means of $^1H$, $^{19}F$, $^{13}C$ and $^{31}P$ NMR spectra.

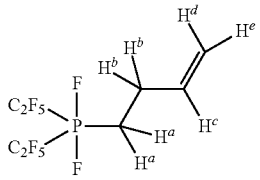

NMR (lock substance: $CD_3CN$ film; δ in ppm)

$^1H$ NMR: 2.35 m ($2H^a$), 2.47 m ($2H^b$), 5.02 d, m $^3J_{H,H}$=10 Hz ($1H^e$), 5.05 d, m $^3J_{H,H}$=17 Hz ($1H^d$), 5.71 d, d, t $^3J_{H,H}$=17 Hz, $^3J_{H,H}$=10 Hz, $^3J_{H,H}$=6 Hz ($1H^c$)

$^{13}C$ NMR: 25.8 t, d, t, m $^1J_{C,H}$=133 Hz, $^3J_{C,F}$=8 Hz, $^2J_{C,P}$=4 Hz ($1C^b$), 29.0 t, d, t, m $^1J_{C,H}$=123 Hz, $^1J_{C,P}$=108 Hz, $^2J_{C,F}$=17 Hz ($1C^a$), 113.3 t, d, q, m $^1J_{C,F}$=284 Hz, $^1J_{C,P}$=86 Hz, $^2J_{C,F}$=42 Hz ($2CF_2$), 116.0 d, d, t, d, m $^1J_{C,H}$=159 Hz, $^1J_{C,H}$=154 Hz, $^3J_{C,H}$=6 Hz, $^4J_{C,P}$=1.5 Hz ($1C^d$), 118.4 q, t, d, m $^1J_{C,F}$=286 Hz, $^2J_{C,F}$=32 Hz, $^2J_{C,P}$=27 Hz ($2CF_3$), 134.6 d, d, m $^1J_{C,H}$=156 Hz, $^3J_{C,P}$=21 Hz ($1C^c$)

$^{19}F$ NMR: −49.7 d, t, q, m $^1J_{F,P}$=876 Hz, $^3J_{F,F}$=14 Hz, $^4J_{F,F}$=11 Hz (2F), −83.6 t $^4J_{F,F}$=11 Hz (6F), −118.0 d, t $^2J_{F,P}$=112 Hz, $^3J_{F,F}$=14 Hz (4F)

$^{31}P$ NMR: −31.5 t, qui, t, t $^1J_{P,F}$=876 Hz, $^2J_{P,F}$=112 Hz, $^2J_{P,H}$=18 Hz, $^3J_{P,H}$=13 Hz (1P).

EXAMPLE 8

Synthesis of bis(pentafluoroethyl)(but-3-en-1-yl) phosphine oxide by Reaction of bis(pentafluoroethyl)(but-3-en-1-yl)difluorophosphorane and hexamethyldisiloxane using Catalytic Amounts of $H_2O$

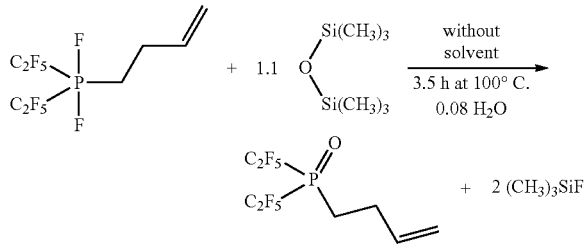

Hexamethyldisiloxane (76.2 g, 469 mmol) and $H_2O$ (619 mg; 34.4 mmol) are added to bis(pentafluoroethyl)(but-3-en-1-yl)difluorophosphorane, $(C_2F_5)_2PF_2$ $(CH_2CH_2CH{=}CH_2)$, from Example 7 (151.4 g, 418 mmol), containing bis(pentafluoroethyl)difluorocyclopropylmethylphosphorane, $(C_2F_5)_2PF_2(CH_2\text{-c-}C_3H_5)$ (5%) and di(but-3-en-1-yl)zinc (3%)] in a 250 ml glass round-bottomed flask, and the mixture is stirred at 100° C. for 3.5 hours with evolution of gas. The product is subsequently condensed at room temperature to 30° C. in vacuo ($10^{-3}$ mbar). Bis(pentafluoroethyl)(but-3-en-1-yl)phosphine oxide, $(C_2F_5)_2P(O)(CH_2CH_2CH{=}CH_2)$ (131.2 g; 386 mmol), can be isolated as a clear and colourless liquid with a yield of 92%. By-products are bis(pentafluoroethyl)cyclopropylmethylphosphine oxide, $(C_2F_5)_2P(O)(CH_2\text{-c-}C_3H_5)$ (5%, 6.8 g; 20 mmol), trimethylfluorosilane and hexamethyldisiloxane (13.7 g). This mixture is used without further purification. The compounds can be separated using methods which are known to the person skilled in the art.

The product, bis(pentafluoroethyl)(but-3-en-1-yl)-phosphine oxide, $(C_2F_5)_2P(O)(CH_2CH_2CH{=}CH_2)$, is characterised by means of $^1H$, $^{13}C$, $^{19}F$ and $^{31}P$ NMR spectra.

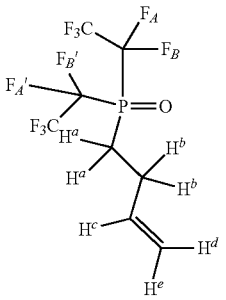

NMR (lock substance: $CDCl_3$; δ in ppm)

$^1H$ NMR: 2.44 m ($2H^a$), 2.56 m ($2H^b$), 5.13 d, d, t $^3J_{H,H}$=10 Hz, $2J_{H,H}$=1.2 Hz, $^4J_{H,H}$=1.0 Hz ($1H^e$), 5.16 d, t, d $^3J_{H,H}$=17 Hz, $^4J_{H,H}$=1.5 Hz, $^2J_{H,H}$=1.2 Hz ($1H^d$), 5.86 d, d, t $^3J_{H,H}$=17 Hz, $^3J_{H,H}$=10 Hz, $^3J_{H,H}$=6 Hz ($1H^c$)

$^{13}C$ NMR: 23.8 t, d, t, m $^1J_{C,H}$=133 Hz, $^1J_{C,P}$=64 Hz, $^2J_{C,H}$=6 Hz ($1C^a$), 24.1 t, t, d, m $^1J_{C,H}$=132 Hz, $^2J_{C,H}$=6 Hz, $^2J_{C,H}$=5 Hz ($1C^b$), 112.9 d, d, d, q, m $^1J_{C,FA}$=$^1J_{C,FA'}$=286 Hz, $^1J_{C,FB}$=$^1J_{C,FB'}$=$^1J_{C,P}$=88 Hz, $^2J_{C,F}$=41 Hz ($2CF_2$), 117.3 d, d, t, d, m $^1J_{C,H}$=160 Hz, $^1J_{C,H}$=154 Hz, $^3J_{C,H}$=6 Hz, $^4J_{C,P}$=0.9 Hz ($1C^d$), 118.4 q, d, d, d, m $^1J_{C,F}$=287 Hz, $^2J_{C,FA}$=$^2J_{C,FA'}$=31 Hz, $^2J_{C,FB}$=$^2J_{C,FB'}$=30 Hz $^2J_{C,P}$=17 Hz ($2CF_3$), 134.9 d, d, t, d, d $^1J_{C,H}$=156 Hz, $^3J_{C,P}$=16 Hz, $^2J_{C,H}$=6 Hz, $^2J_{C,H}$=3 Hz, $^2J_{C,H}$=3 Hz ($1C^c$)

$^{19}F$ NMR: −80.3 d, m $^3J_{F,P}$=1.2 Hz (6F), −121.7 d, m $^2J_{FA,P}$=77 Hz, $^2J_{FB,P}$=69 Hz, $^2J_{FA,FB}$=340 Hz ($2F_A$), −123.6 d, m $^2J_{FA',P}$=77 Hz, $^2J_{FB',P}$=69 Hz, $^2J_{FA',FB'}$=310 Hz ($2F_B$)

$^{31}P$ NMR: 37.8 t, t, t, t, sep $^2J_{P,FA}$=$^2J_{P,FA'}$=77 Hz, $^2J_{P,FB}$=$^2J_{P,FB'}$=69 Hz, $^2J_{P,H}$=10 Hz , $^3J_{P,H}$=10 Hz, $^3J_{P,F}$=1.2 Hz (1P).

EXAMPLE 9

Synthesis of (but-3-en-1-yl)(pentafluoroethyl)phosphinic acid by Hydrolysis of bis(pentafluoroethyl)(but-3-en-1-yl)phosphine oxide

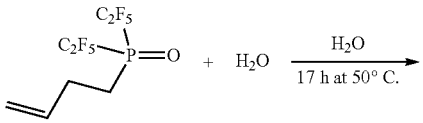

-continued

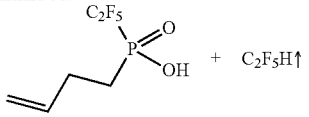

Bis(pentafluoroethyl)(but-3-en-1-yl)phosphine oxide, $(C_2F_5)_2P(O)$—$(CH_2CH_2CH{=}CH_2)$ (130.3 g, 383 mmol), from Example 8 is emulsified with water (100 ml) in a 250 ml glass round-bottomed flask and warmed (50° C.). The emulsion is stirred at 50° C. for 17 hours with constant evolution of gas. All volatile constituents are subsequently condensed off at room temperature in vacuo ($10^{-3}$ mbar). The product which remains is distilled at 130° C. in vacuo ($10^{-3}$ mbar). (Pentafluoroethyl)(but-3-en-1-yl)phosphinic acid, $(C_2F_5)$—$(CH_2CH_2CH{=}CH_2)P(O)OH$ (89.7 g; 375 mmol), can be isolated as a clear and colourless liquid (94.0 g) with a yield of 93%. The only by-product is pentafluoroethyl(cyclopropylmethyl)phosphinic acid, $(C_2F_5)(CH_2\text{-c-}C_3H_5)$—$P(O)OH$ (4.3 g; 18 mmol), which results from bis(pentafluoroethyl)cyclopropylmethylphosphine oxide in the starting material. The two compounds can be separated using methods which are known to the person skilled in the art. The isolated product is characterised by means of $^1H$, $^{13}C$, $^{19}F$ and $^{31}P$ NMR spectra.

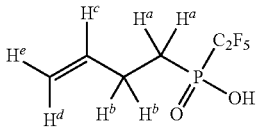

NMR (lock substance: $CDCl_3$; δ in ppm)

$^1H$ NMR: 2.02 m ($2H^a$), 2.41 m ($2H^b$), 5.06 d, t, d $^3J_{H,H}$=10 Hz, $^4J_{H,H}$=1.4 Hz, $^2J_{H,H}$=1.1 Hz ($1H^e$), 5.10 d, t, d $^3J_{H,H}$=17 Hz, $^4J_{H,H}$=1.4 Hz, $^2J_{H,H}$=1.2 Hz ($1H^d$), 5.83 d, d, t $^3J_{H,H}$=17 Hz, $^3J_{H,H}$=10 Hz, $^3J_{H,H}$=6 Hz ($1H^c$), 10.86 s $\Delta v_{1/2}$=7 Hz (1OH)

$^{13}C$ NMR: 24.5 t, d, m $^1J_{C,H}$=129 Hz, $^2J_{C,P}$=5 Hz ($1C^b$), 25.1 t, d, m $^1J_{C,H}$=129 Hz, $^1J_{C,P}$=102 Hz ($1C^a$), 111.6 t, d, q $^1J_{C,F}$=276 Hz, $^1J_{C,P}$=127 Hz, $^2J_{C,F}$=40 Hz, ($1CF_2$), 116.5 d, d, t $^1J_{C,H}$=159 Hz, $^1J_{C,H}$=154 Hz, $^3J_{C,H}$=6 Hz ($1C^d$), 119.0 q, t, d $^1J_{C,F}$=286 Hz, $^2J_{C,F}$=31 Hz, $^2J_{C,P}$=16 Hz ($1CF_3$), 136.3 d, d, t, d, d $^1J_{C,H}$=155 Hz, $^3J_{C,P}$=17 Hz, $^2J_{C,H}$=6 Hz, $^2J_{C,H}$=3 Hz, $^2J_{C,H}$=3 Hz ($1C^c$)

$^{19}F$ NMR: −80.8 s $\Delta v_{1/2}$=5 Hz (3F), −121.5 d $^2J_{F,P}$=81 Hz (2F)

$^{31}P$ NMR: 34.5 t $^2J_{P,F}$=81 Hz (1P).

EXAMPLE 10

Synthesis of undec-10-en-1-ylmagnesium bromide by Reaction of 11-bromo-1-undecene and Magnesium

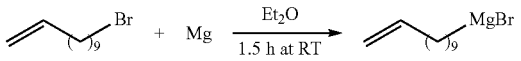

Magnesium turnings (0.53 mg, 21.6 mmol) in diethyl ether (20 ml) are initially introduced in a 100 ml glass round-bottomed flask, and 11-bromo-1-undecene (5.25 g, 22.5 mmol) in diethyl ether (20 ml) is added over the course of 1 hour. The yellow suspension is stirred at room temperature for 30 minutes and subsequently filtered. Undec-10-en-1-ylmagnesium bromide (83%, ~18 mmol) in diethyl ether can be obtained as a yellow solution. By-product is 1,21-docosadiene (11 mol %). This solution is used without further purification. The isolated product is characterised by means of 1H and $^{13}C$ NMR spectra.

NMR (lock substance: $CD_3CN$ film; δ in ppm)

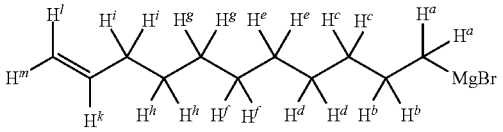

$^1H$ NMR: −0.54 t $^3J_{H,H}$=8 Hz (2H$^a$), 1.26-1.29° t$^3J_{H,H}$=7 Hz (10H$^{c-g}$), 1.36° t, t $^3J_{H,H}$=7 Hz, $^3J_{H,H}$=7 Hz (2H$^h$), 1.50 t, t $^3J_{H,H}$=7 Hz, $^3J_{H,H}$=7 Hz (2H$^b$), 2.01 t, d, t $^3J_{H,H}$=7 Hz, 3$J_{H,H}$=7 Hz, $^4J_{H,H}$=1 Hz (2H$^i$), 4.86 d, d, t, t $^3J_{H,H}$=10 Hz, $^2J_{H,H}$=2 Hz, $^4J_{H,H}$=1 Hz, $^5J_{H,H}$=1 Hz (1H$^m$), 4.93 d, d, t $^3J_{H,H}$=17 Hz, $^2J_{H,H}$=2 Hz, $^4J_{H,H}$=2 Hz (1H$^l$), 5.75 d, d, t $^3J_{H,H}$=17 Hz, $^3J_{H,H}$=10 Hz, $^3J_{H,H}$=7 Hz (1H$^k$)

$^{13}C\{^1H\}$ NMR: 8.5 (1C$^a$), 29.7 (1C$^{b,d-h}$), 29.9 (1C$^{b,d-h}$), 30.3° (1C$^{b,d-h}$), 30.4° (1C$^{b,d-h}$), 30.4° (1C$^{b,d-h}$), 30.6 (1C$^{b,d-h}$), 34.5 (1C$^i$), 39.0 (1C$^c$), 114.2 (1C$^l$), 139.4 (1C$^k$).

° signals superimposed

EXAMPLE 11

Synthesis of bis(undec-10-en-1-yl)zinc by Reaction of undec-10-en-1-ylmagnesium bromide and Zinc Chloride

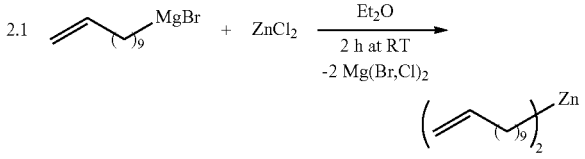

Zinc chloride, $ZnCl_2$ (2.99 g, 21.9 mmol), is suspended in diethyl ether (40 ml) in a 250 ml glass round-bottomed flask, and a solution of undec-10-en-1-ylmagnesium bromide (45.2 mmol, contains 17 mol % of 1,21-docosadiene) in diethyl ether (120 ml) is added over the course of 45 minutes. A bulky white solid rapidly precipitates out. The suspension is filtered under inert gas, and the residue is washed with diethyl ether (10 ml). The pale-yellow filtrate is evaporated together with the wash solution at room temperature in vacuo ($10^{-3}$ mbar). The bulky suspension formed is extracted three times with n-pentane (20 ml each time) and filtered under inert conditions. The n-pentane phases are subsequently combined, and n-pentane is condensed off at 40° C. in vacuo ($10^{-3}$ mbar). Di(undec-10-en-1-yl)zinc (6.17 g, 16.6 mmol) can be isolated as a clear and yellow liquid with a yield of 76%. The only by-product is 1,21-docosadiene (3.18 g, 10.4 mmol, 39 mol %). The two compounds can be separated using methods which are known to the person skilled in the art. This solution is used without further purification. The product, di(undec-10-en-1-yl)zinc, is characterised by means of $^1H$ and $^{13}C$ NMR spectra.

NMR (lock substance: $CD_3CN$ film; δ in ppm)

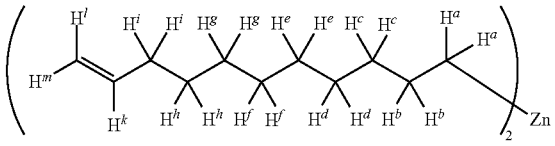

$^1H$ NMR: 0.39 t $^3J_{H,H}$=8 Hz (4H$^a$), 1.26-1.28° t $^3J_{H,H}$=7 Hz (20H$^{c-g}$), 1.36° t, t $^3J_{H,H}$=7 Hz, $^3J_{H,H}$=7 Hz (4H$^h$), 1.55 t, t $^3J_{H,H}$=7 Hz, $^3J_{H,H}$=7 Hz (4H$^b$), 2.00 t, d $^3J_{H,H}$=7 Hz, $^3J_{H,H}$=7 Hz (4H$^i$), 4.87 d, d, t $^3J_{H,H}$=10 Hz, $^2J_{H,H}$=2 Hz, $^4J_{H,H}$=1 Hz (2H$^m$), 4.93 d, d, t $^3J_{H,H}$=17 Hz, $^2J_{H,H}$=2 Hz, $^4J_{H,H}$=2 Hz (2H$^l$), 5.73 d, d, t $^3J_{H,H}$=17 Hz, $^3J_{H,H}$=10 Hz, $^3J_{H,H}$=7 Hz (2H$^k$)

$^{13}C$ NMR: 16.8 t, m $^1J_{C,H}$=120 Hz (2C$^a$), 26.9 t, m $^1J_{C,H}$=124 Hz (2C$^b$), 29.5° t, m $^1J_{C,H}$=126 Hz (2C$^{d-h}$), 29.8° t, m $^1J_{C,H}$=126 Hz (2C$^{d-h}$), 30.2° t, m $^1J_{C,H}$=126 Hz (2C$^{d-h}$), 30.3° t, m $^1J_{C,H}$=126 Hz (2C$^{d-h}$), 30.4° t, m $^1J_{C,H}$=126 Hz (2C$^{d-h}$), 34.4 t, m $^1J_{C,H}$=126 Hz (2C$^i$), 37.1 t, m $^1J_{C,H}$=124 Hz (2C$^c$), 114.6 d, d, t $^1J_{C,H}$=157 Hz, $^1J_{C,H}$=153 Hz, $^3J_{C,H}$=6 Hz (2C$^l$), 139.0 d, d, d, t $^1J_{C,H}$=150 Hz, $^2J_{C,H}$=6 Hz, $^2J_{C,H}$=6 Hz, $^2J_{C,H}$=6 Hz (2C$^K$).

* signals broadened

° signals superimposed

EXAMPLE 12

Synthesis of bis(pentafluoroethyl)difluoro(undec-10-en-1-yl)phosphorane by Reaction of di(undec-10-en-1-yl)zinc and bis(pentafluoroethyl)trifluorophosphorane

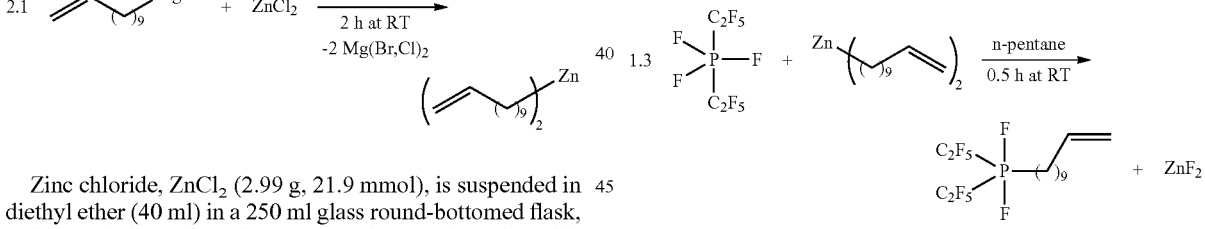

Di(undec-10-en-1-yl)zinc (2.39 g, 6.43 mmol; additionally contains 1.53 g of 1,21-docosadiene) is dissolved in n-pentane (40 ml) in a 100 ml glass round-bottomed flask. Bis(pentafluoroethyl)trifluorophosphorane, $(C_2F_5)_2PF_3$ (2.54 g, 7.79 mmol), is added to this solution over the course of 10 minutes. The solution is stirred at room temperature for 30 minutes. A suspension forms. The conversion (96%, 7.48 mmol) to bis(pentafluoroethyl)difluoro(undec-10-en-1-yl) phosphorane, $(C_2F_5)_2PF_2(C_9H_{18}CH{=}CH_2)$, is virtually quantitative. The only by-product formed besides $ZnF_2$ is bis(pentafluoroethyl)(cyclopropyloctyl)difluorophosphorane, $(C_2F_5)_2PF_2(C_8H_{16}$-cyclo-$C_3H_5)$ (4%). In addition, 1,21-docosadiene from the starting material (see Example 10) are also in the suspension. The compounds can be separated using methods which are known to the person skilled in the art. The suspension is used here without further purification. The product is characterised by means of $^1H$, $^{13}C\{^1H\}$, $^{19}F$ and $^{31}P$ NMR spectra.

NMR (lock substance: $CD_3CN$ film; δ in ppm)

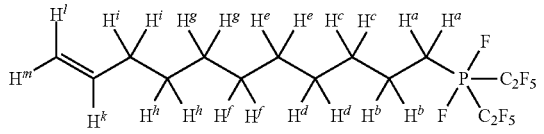

$^{1}$H NMR: 1.28-1.31° s (10H$^{c-g}$), 1.37° t, t $^{3}J_{H,H}$=7 Hz, $^{3}J_{H,H}$=7 Hz (2H$^{h}$), 1.66 d, t, t $^{3}J_{H,P}$=13 Hz, $^{3}J_{H,H}$=7 Hz, $^{3}J_{H,H}$=7 Hz (2H$^{b}$), 2.02 t, d, t, D $^{3}J_{H,H}$=7 Hz, $^{3}J_{H,H}$=7 Hz, $^{4}J_{H,H}$=1.6 Hz, $^{4}J_{H,H}$=1.2 Hz (2H$^{i}$), 2.37 d, t, t $^{2}J_{H,P}$=18 Hz, $^{3}J_{H,F}$=17 Hz, $^{3}J_{H,H}$=7 Hz (2H$^{a}$), 4.87 d, d, t, t $^{3}J_{H,H}$=10 Hz, $^{2}J_{H,H}$=1.9 Hz, $^{4}J_{H,H}$=1.2 Hz, $^{5}J_{H,H}$=0.9 Hz (1H$^{m}$), 4.94 d, d, t $^{3}J_{H,H}$=17 Hz, $^{2}J_{H,H}$=1.9 Hz, $^{4}J_{H,H}$=1.6 Hz (1H$^{l}$), 5.74 d, d, t $^{3}J_{H,H}$=17 Hz, $^{3}J_{H,H}$=10 Hz, $^{3}J_{H,H}$=7 Hz (1H$^{k}$)

$^{13}$C{$^{1}$H} NMR: 22.1 t, d $^{3}J_{C,F}$=7 Hz, $^{2}J_{C,P}$=6 Hz (1C$^{b}$), 29.0 d $^{3}J_{C,P}$=1.7 Hz (1C$^{c}$), 29.3 (1C$^{d-h}$), 29.5° (1C$^{d-h}$), 29.5° (1C$^{d-h}$), 30.0° d, t $^{1}J_{C,P}$=91 Hz, $^{2}J_{C,F}$=17 Hz (1C$^{a}$), 30.0° (1C$^{d-h}$), 30.1° (1C$^{d-h}$), 34.1 (1C$^{i}$), 114.0 (1C$^{l}$), 138.7 (1C$^{k}$), n.b. (2C$_2$F$_5$)

$^{19}$F NMR: −49.4 d, t, qui, sep $^{1}J_{F,P}$=875 Hz, $^{3}J_{F,H}$=17 Hz, $^{3}J_{F,F}$=14 Hz, $^{4}J_{F,F}$=11 Hz (2F), −82.7 t $^{4}J_{F,F}$=11 Hz (6F), −117.5 d, t $^{2}J_{F,P}$=111 Hz, $^{3}J_{F,F}$=14 Hz (4F)

$^{31}$P NMR: −30.9 t, qui, t, t $^{1}J_{P,F}$=875 Hz, $^{2}J_{P,F}$=111 Hz, $^{2}J_{P,H}$=18 Hz, $^{3}J_{P,H}$=13 Hz (1P).

° signals superimposed

EXAMPLE 13

Synthesis of bis(pentafluoroethyl)(undec-10-en-1-yl)-phosphine oxide by Reaction of bis(pentafluoroethyl)(undec-10-en-1-yl)difluorophosphorane and Hexamethyldisiloxane

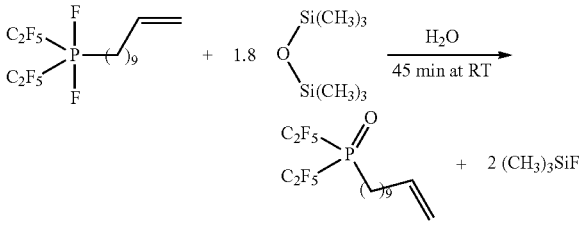

The suspension from Example 12 consisting of bis(pentafluoroethyl)(undec-10-en-1-yl)difluorophosphorane, $(C_2F_5)_2PF_2(C_9H_{18}CH{=}CH_2)$ (7.48 mmol) in n-pentane (40 ml) (additionally contains bis(pentafluoroethyl)(cycloprop-8-yloctyl)difluorophosphorane, $(C_2F_5)_2PF_2(C_8H_{16}$-cyclo-$C_3H_5)$ (4%) and ZnF2) is initially introduced in a 100 ml glass round-bottomed flask, and n-pentane is distilled off at 80° C. Hexamethyldisiloxane (2.32 g, 14.3 mmol) and water (2 g, 110 mmol) is subsequently added and stirred at room temperature for 45 minutes. A conversion of 88% to bis(pentafluoroethyl)(undec-10-en-1-yl)phosphine oxide, $(C_2F_5)_2P(O)(C_9H_{18}CH{=}CH_2)$, can be detected in the yellow mother liquor. By-products are bis(pentafluoroethyl)(cycloprop-8-yl-octyl)phosphine oxide, $(C_2F_5)_2P(O)(C_8H_{16}$-cyclo-$C_3H_5)$ (4 mol %), which results from bis(pentafluoroethyl)(cycloprop-8-yloctyl) difluorophosphorane in the starting material, and (pentafluoroethyl)(undec-10-en-1-yl)phosphinic acid, $(C_2F_5)(C_9H_{18}CH{=}CH_2)P(O)OH$ (8 mol %). In addition, undecene, $ZnF_2$ and 1,21-docosadiene are also from the starting material (see Example 11). The compounds can be separated using methods which are known to the person skilled in the art. The suspension is used here without further purification. The product is characterised by means of $^{1}$H, $^{13}$C{$^{1}$H}, $^{19}$F and $^{31}$P NMR spectra.

NMR (lock substance: $CD_3CN$ film, δ in ppm)

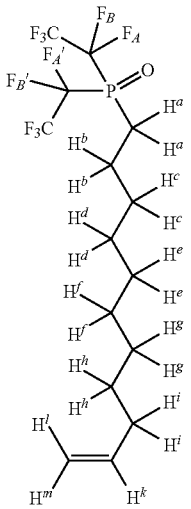

$^{1}$H NMR: 1.28-1.30° s (8H$^{d-g}$), 1.38° t, t $^{3}J_{H,H}$=7 Hz, $^{3}J_{H,H}$=7 Hz (2H$^{h}$), 1.47 t, t $^{3}J_{H,H}$=7 Hz, $^{3}J_{H,H}$=6 Hz, (2H$^{c}$), 1.78 d, t, t $^{3}J_{H,P}$=10 Hz, $^{3}J_{H,H}$=8 Hz, $^{3}J_{H,H}$=8 Hz (2H$^{b}$), 2.02 t, d, t, d $^{3}J_{H,H}$=7 Hz, $^{3}J_{H,H}$=7 Hz, $^{4}J_{H,H}$=1 Hz, $^{4}J_{H,H}$=1 Hz (2H$^{i}$), 2.29 d, t $^{2}J_{H,P}$=11 Hz, $^{3}J_{H,H}$=8 Hz (2H$^{a}$), 4.87 d, d, t, t $^{3}J_{H,H}$=10 Hz, $^{2}J_{H,H}$=2 Hz, $^{4}J_{H,H}$=1 Hz, $^{5}J_{H,H}$=1 Hz (1H$^{m}$), 4.94 d, d, t $^{3}J_{H,H}$=17 Hz, $^{2}J_{H,H}$=2 Hz, $^{4}J_{H,H}$=2 Hz (1H$^{l}$), 5.74 d, d, t $^{3}J_{H,H}$=17 Hz, $^{3}J_{H,H}$=10 Hz, $^{3}J_{H,H}$32 7 Hz (1H$^{k}$)

$^{13}$C{$^{1}$H} NMR: 20.1 d $^{2}J_{C,P}$=5 Hz (1C$^{b}$), 24.1 d $^{1}J_{C,P}$=61 Hz (1C$^{a}$), 29.1 d $^{4}J_{C,P}$=0.8 Hz (1C$^{d}$), 29.2 (1C$^{e-h}$), 29.6 (1C$^{e-h}$), 30.0° (1C$^{e-h}$), 30.1° (1C$^{e-h}$), 30.9 d $^{3}J_{C,P}$=15 Hz (1C$^{c}$), 34.1 (1C$^{i}$), 112.9 t, m $^{1}J_{C,F}$=286 Hz (2CF$_2$), 114.3 (1C$^{l}$), 118.4 q, m $^{1}J_{C,F}$=287 Hz (2CF$_3$), 138.6 (1C$^{k}$)

$^{19}$F NMR: −80.0 d $^{3}J_{F,P}$=3 Hz (6F), −121.5 d, m $^{2}J_{FA,P}$=75 Hz, $^{2}J_{FB,P}$=66 Hz, $^{2}J_{FA,FB}$=340 Hz (2F$_A$), −123.5 d, m, $^{2}J_{FA',P}$=75 Hz, $^{2}J_{FB',P}$=66 Hz, $^{2}J_{FA',FB'}$=310Hz (2F$_B$)

$^{31}$P NMR: 37.6 t, t, t, t $^{2}J_{P,FA}$=$^{2}J_{P,FA'}$=75 Hz, $^{2}J_{P,FB}$=$^{2}J_{P,FB'}$=66 Hz, $^{2}J_{P,H}$=11 Hz, $^{3}J_{P,H}$=10 Hz (1P).

° signals superimposed

EXAMPLE 14

Synthesis of pentafluoroethyl(undec-10-en-1-yl) phosphinic acid by Hydrolysis of bis(pentafluoroethyl)(undec-10-en-1-yl)-phosphine oxide

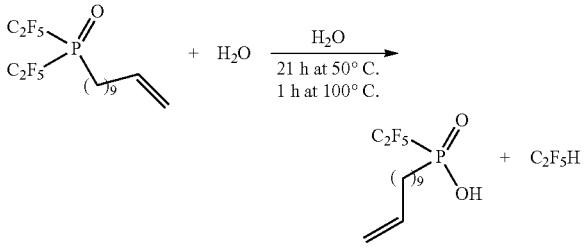

Water (7 g, 390 mmol) is added to the suspension from Example 13, bis-(pentafluoroethyl)(undec-10-en-1-yl)phosphine oxide, $(C_2F_5)_2P(O)—(C_9H_{18}CH{=}CH_2)$ [besides undecene, $ZnF_2$ and 1,21-docosadiene, additionally contains bis(pentafluoroethyl)(cycloprop-8-yloctyl)phosphine oxide, $(C_2F_5)_2P(O)(C_8H_{16}\text{-}C\text{-}C_3H_5)$ (4 mol %), and pentafluoroethyl(undec-10-en-1-yl)phosphinic acid, $(C_2F_5)(C_9H_{18}CH{=}CH_2)P(O)OH$ (8 mol %)], in a 250 ml glass round-bottomed flask and warmed (50° C.). This emulsion is stirred at 50° C. for 21 hours and at 100° C. for 1 hour. The emulsion is subsequently extracted with hot n-pentane (60 ml) and n-hexane (60 ml) under reflux. The organic phases are combined and washed with water (10 ml). All volatile constituents from the organic phase are removed at room temperature to 90° C. in vacuo ($10^{-3}$ mbar). Pentafluoroethyl(undec-10-en-1-yl)-phosphinic acid, $(C_2F_5)(C_9H_{18}CH{=}CH_2)P(O)OH$ (2.32 g, 6.9 mmol), can be isolated as a yellow solid with a yield of 88%. By-products are pentafluoroethyl(cycloprop-8-yloctyl)phosphinic acid, $(C_2F_5)(C_8H_{16}\text{-cyclo-}C_3H_5)P(O))OH$ (4%), and 1,21-docosadiene from Example 12. The compounds can be removed using methods which are known to the person skilled in the art. The product is characterised by means of $^1H$, $^{13}C\{^1H\}$, $^{19}F$ and $^{31}P$ NMR spectra.

NMR (lock substance: toluene-d8; δ in ppm)

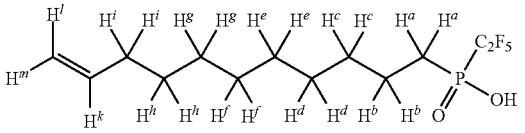

$^1H$ NMR: 1.27-1.32° s ($10H^{c-g}$), 1.36° t $^3J_{H,H}$=7 Hz ($2H^h$), 1.83*° s ($2H^b$), 1.99° t, d, t, $^3J_{H,H}$=7 Hz, $^3J_{H,H}$=7 Hz, $^4J_{H,H}$=1 Hz ($2H^i$), 2.05*° d, t $^2J_{H,P}$=12 Hz, $^3J_{H,H}$=7 Hz ($2H^a$), 4.97 d, d, t $^3J_{H,H}$=10 Hz, $^2J_{H,H}$=2 Hz, $^4J_{H,H}$=1 Hz ($1H^m$), 5.02 d, d, t $^3J_{H,H}$=17 Hz, $^2J_{H,H}$=2 Hz, $^4J_{H,H}$=2 Hz ($1H^l$), 5.78 d, d, t $^3J_{H,H}$=17 Hz, $^3J_{H,H}$=10 Hz, $^3J_{H,H}$=7 Hz ($1H^k$), 13.01 s ($^1H^n$)

$^{13}C\{^1H\}$ NMR: 23.6* ($1C^b$), 25.9* d $^1J_{C,P}$=103 Hz ($1C^a$), 29.8° d $^4J_{C,P}$=0.9 Hz ($1C^d$), 29.8° ($1C^{e-h}$), 29.9 ($1C^{e-h}$), 30.1 ($1C^{e-h}$), 30.3 ($1C^{e-h}$), 31.2 d $^3J_{C,P}$=16 Hz ($1C^c$), 34.7 ($1C^i$), 114.9 ($1C^l$), 139.5 ($1C^k$), n.b. ($1C_2F_5$)

$^{19}F$ NMR: −80.5 s (3F), −127.3 d $^2J_{F,P}$=79 Hz (2F)

$^{31}P$ NMR: −35.7 t, t, t $^2J_{P,F}$=79 Hz, $^2J_{P,H}$=12 Hz, $^3J_{P,H}$=12 Hz (1P).

* signals broadened

° signals superimposed

EXAMPLE 15

Synthesis of 4-styrylmagnesium Chloride by Reaction of 4-chlorostyrene and Magnesium

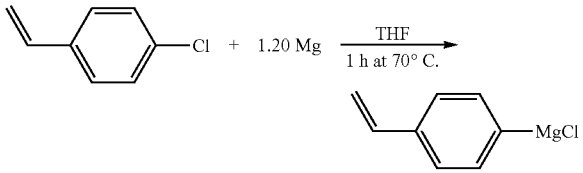

Magnesium turnings (1.78 g, 73.2 mmol) are suspended in tetrahydrofuran (20 ml) in a 100 ml glass round-bottomed flask and activated using bromoethane, $C_2H_5Br$ (1.16 g, 10.6 mmol). After 10 minutes, the THF mother liquor is decanted. The activated magnesium turnings (1.52 g, 62.6 mmol) are re-suspended in THF (60 ml), 4-chlorostyrene (7.24 g, 52.2 mmol) is added and warmed (70° C.). After 1 hours at 70° C., a brown-black suspension can be obtained. The conversion to 4-styrylmagnesium chloride is 98%. The brown-black THF mother liquor can be stored cooled (0° C.) for some time. The product is characterised by $^1H$ and $^{13}C$ NMR spectra.

NMR (lock substance: $CD_3CN$ film; δ in ppm)

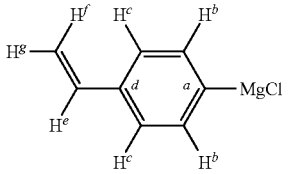

$^1H$ NMR: 4.96 d, d $^3J_{H,H}$=11 Hz, $^2J_{H,H}$=1.6 Hz ($1H^g$), 5.62 d, d $^3J_{H,H}$=18 Hz, $^2J_{H,H}$=1.6 Hz ($1H^f$), 6.62 d, d $^3J_{H,H}$=18 Hz, $^3J_{H,H}$=11 Hz ($1H^e$), 7.10 d $^3J_{H,H}$=8 Hz ($2H^c$), 7.71 d $^3J_{H,H}$=8 Hz ($2H^b$)

$^{13}C$ NMR: 108.7 d, d $^1J_{C,H}$=159 Hz, $^1J_{C,H}$=154 Hz ($1C^f$), 123.4 d, d, d, d, m $^1J_{C,H}$=151 Hz, $^3J_{C,H}$=5 Hz, $^3J_{C,H}$=4 Hz, $^4J_{C,H}$=4 Hz ($2C^c$), 133.1 m ($1C^d$), 139.6 d, t, d, m $^1J_{C,H}$=150 Hz, $^3J_{C,H}$=5 Hz, $^2J_{C,H}$=3 Hz ($1C^e$), 140.8 d, d, m $^1J_{C,H}$=151 Hz, $^2J_{C,H}$=12 Hz ($2C^b$), 172.2 m ($1C^a$).

EXAMPLE 16

Synthesis of di(4-styryl)zinc by Reaction of 4-styrylmagnesium Chloride and Zinc Chloride

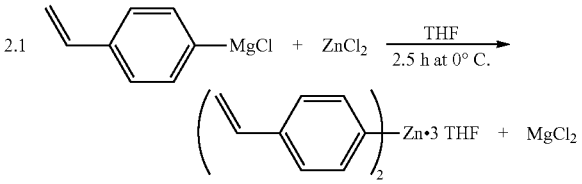

4-Styrylmagnesium chloride (51.2 mmol) in tetrahydrofuran (60 ml) from Example 15 is initially introduced in a 100 ml glass round-bottomed flask and cooled (0° C.). Zinc chloride, $ZnCl_2$ (3.35 g, 24.6 mmol), is added to this THF solution. The suspension is stirred at 0° C. for 2.5 hours and subsequently centrifuged. The yellow mother liquor is decanted into a 100 ml glass round-bottomed flask and THF is condensed off at 0° C. in vacuo ($10^{-3}$ mbar). A white solid remains behind. This is extracted three times with toluene (50 ml each time). Toluene is condensed off from the combined toluene phases at 0° C. in vacuo ($10^{-3}$ mbar) in a 250 ml glass round-bottomed flask. Since THF can still be detected in the resultant white solid, the solid is suspended two further times in toluene (20 ml each time). All volatile compounds are subsequently condensed off again at 0° C. in vacuo ($10^{-3}$ mbar). Distyrylzinc-3THF (6.84 g, 14.0 mmol) can be isolated as a white solid with a yield of 57%. The isolated product is characterised by means of $^1H$ and $^{13}C$ NMR spectra.

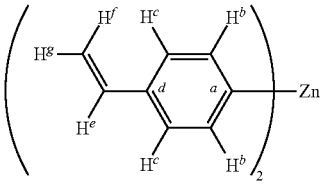

NMR (lock substance: $CD_3CN$; δ in ppm)

$^1H$ NMR: 5.11 d $^3J_{H,H}$=11 Hz (2H$^g$), 5.73 d $^3J_{H,H}$=18 Hz (2H$^f$), 6.71 d, d $^3J_{H,H}$=18 Hz, $^3J_{H,H}$=11 Hz (2H$^e$), 7.25 d $^3J_{H,H}$=8 Hz (4H$^c$), 7.59 d $^3J_{H,H}$=8 Hz (4H$^b$)

$^{13}C$ NMR: 111.7 d, d $^1J_{C,H}$=159 Hz, $^1J_{C,H}$=155 Hz (2C$^f$), 125.0 d $^1J_{C,H}$=153 Hz (4C$^c$), 133.9 m (2C$^d$), 139.2 d $^1J_{C,H}$=152 Hz (2C$^e$), 139.6 d, d $^1J_{C,H}$=156 Hz, $^2J_{C,H}$=11 Hz (4C$^b$), 160.5 m (2C$^a$).

EXAMPLE 17

Synthesis of pentafluoroethyl)tetrafluorophosphorane

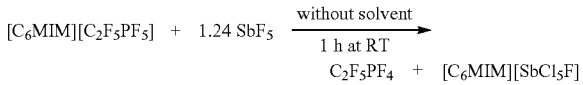

Pale-yellow hexylmethylimidazolium pentafluoroethylpentafluorophosphate, $[C_6MIM][C_2F_5PF_5]$ (10.52 g, 25.52 mmol), is initially introduced in a 10 ml glass reactor with J. Young tap, cooled (−78° C.), and antimony pentafluoride, $SbF_5$ (6.88 g, 31.74 mmol) is added. The reaction solution is warmed (RT), during which an emulsion forms. After 1.5 h at RT, pentafluoroethyltetrafluorophosphorane, $C_2F_5PF_4$, is formed quantitatively as a very volatile clear and colourless liquid. The product is used directly without purification for subsequent experiments. Isolated product can be characterised by means of $^{19}F$ and $^{31}P$ NMR spectra.

NMR (lock substance: $CD_3CN$ film; δ in ppm)

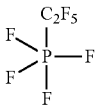

$^{19}F$ NMR: −60.1 d, t, q $^1J_{F,P}$=1090 Hz, $^3J_{F,F}$=8 Hz, $^4J_{F,F}$=6 Hz (4F), −84.7 qui, d $^4J_{F,F}$=6 Hz, $^3J_{F,P}$=4 Hz (3F), −120.7 d, qui $^2J_{F,P}$=125 Hz, $^3J_{F,F}$=8 Hz (2F)

$^{31}P$ NMR: −61.2 qui, t $^1J_{P,F}$=1091 Hz, $^2J_{P,F}$=125 Hz (1P).

EXAMPLE 18

Synthesis of pentafluoroethyl-(4-styryl)trifluorophosphorane by Reaction of di(4-styryl)zinc and pentafluoroethyltetrafluorophosphorane

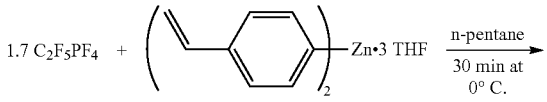

-continued

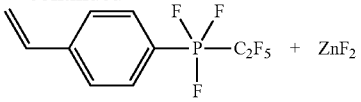

Di(4-styryl)zinc-3THF (6.60 g, 13.5 mmol) is suspended in n-pentane (100 ml) in a 250 ml glass round-bottomed flask with subsequent cooled (−80° C.) condenser and cooled (0° C.). Pentafluoroethyltetrafluorophosphorane, $C_2F_5PF_4$ (5.06 g, 22.4 mmol), is condensed into this suspension over the course of 15 minutes. The yellow suspension is stirred at 0° C. for a further 15 min and, when conversion is complete, warmed to room temperature. The suspension is subsequently centrifuged, and the pink-coloured mother liquor is decanted. The yield of pentafluoroethyl-(4-styryl)trifluorophosphorane, $C_2F_5PF_3$ ($C_6H_4CH{=}CH_2$), in n-pentane is 49%. The product is characterised in n-pentane by means of $^1H$, $^{13}C$, $^{19}F$ and $^{31}P$ NMR spectra.

NMR (lock substance: $CD_3CN$ film; δ in ppm)

$^1H$ NMR: 5.41 d $^3J_{H,H}$=11 Hz (1H$^g$), 5.88 d $^3J_{H,H}$=18 Hz (1H$^f$), 6.70 d, d $^3J_{H,H}$=18 Hz, $^3J_{H,H}$=11 Hz (1H$^e$), 7.47 d, d $^3J_{H,H}$=8 Hz, $^4J_{H,P}$=6 Hz (2H$^c$),

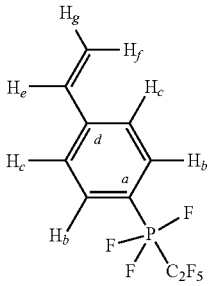

8.04 d, d, m $^3J_{H,P}$=15 Hz, $^3J_{H,H}$=8 Hz (2H$^b$)

$^{13}C$ NMR: 118.5 d, d $^1J_{C,H}$=162 Hz, $^1J_{C,H}$=155 Hz (1C$^f$), 127.3 d, d, d, d $^1J_{C,H}$=161 Hz, $^3J_{C,P}$=19 Hz, $^2J_{C,H}$=6 Hz, $^3J_{C,H}$=6 Hz (2C$^c$), 136.0 d, m $^1J_{C,H}$=157 Hz (1C$^e$), 138.8 d, d, q, m $^1J_{C,H}$=166 Hz, $^2J_{C,P}$=15 Hz, $^3J_{C,F}$=7 Hz (2C$^b$), 145.8 m (1C$^d$), n.d. (1C$^a$), n.d. (1$C_2F_5$)

$^{19}F$ NMR: −70.5* s (3F), −82.3 t, d, q $^4J_{F,F}$=7 Hz, $^3J_{F,P}$=7 Hz, $^3J_{F,F}$=2 Hz (3F), −118.6 d, q, q $^2J_{F,P}$=116 Hz, $^3J_{F,F}$=12 Hz, $^3J_{F,f}$=2 Hz (2F)

$^{31}P$ NMR: −40.5 q, t, t, t, $^1J_{P,F}$=965 Hz, $^2J_{P,F}$=116 Hz, $^3J_{P,H}$=15 Hz, $^4J_{P,H}$=6 Hz (1P).

* signals broadened

EXAMPLE 19

Synthesis of pentafluoroethyl-(4-styryl)phosphinic acid by Hydrolysis of pentafluoroethyl-(4-styryl)trifluorophosphorane using Hexamethyldisiloxane and Water

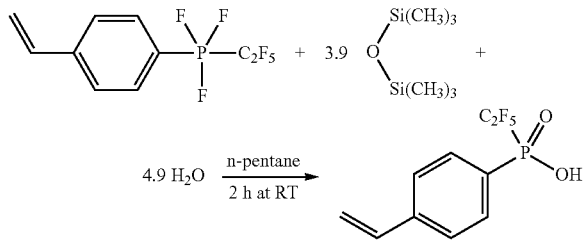

Hexamethyldisiloxane (7.35 g, 45.3 mmol) and water (1.02 g, 56.6 mmol) are added to pentafluoroethyl-(4-styryl) trifluorophosphorane, $(C_2F_5)$-$(4\text{-}C_6H_4CH{=}CH_2)PF_3$ (11.2 mmol), in n-pentane (100 ml) from Example 18 in a 250 ml glass round-bottomed flask. A colourless emulsion resulted. After 2.5 hours at room temperature, the upper n-pentane phase contained neither $(C_2F_5)(4\text{-}C_6H_4CH{=}CH_2)PF_3$ nor product. The n-pentane phase was decanted, the lower phase was suspended in water (10 ml) and washed twice with n-pentane (10 ml each time). The small proportion of solid is filtered off and all volatile constituents of the mother liquor are condensed off at room temperature in vacuo ($10^{-3}$ mbar). Pentafluoroethyl-(4-styryl)phosphinic acid, $(C_2F_5)(CH_2{=}CH{-}C_6H_4)P(O)OH{\cdot}0.5H_2O$ (3.32 g, 11.2 mmol), can be isolated as a beige tacky solid with quantitative yield. The isolated product is characterised by means of $^1H$ and $^{13}C$ NMR spectra.

NMR (lock substance: $CD_3CN$; δ in ppm)

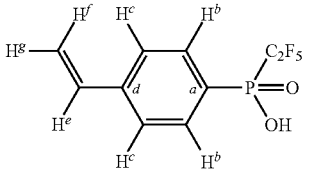

$^1H$ NMR: 5.49 d $^3J_{H,H}$=11 Hz (1H$^g$), 6.00 d $^3J_{H,H}$=18 Hz (1H$^f$), 6.83 d, d $^3J_{H,H}$=18 Hz, $^3J_{H,H}$=11 Hz (1H$^e$), 7.63 d, d $^3J_{H,H}$=8 Hz, $^4J_{H,P}$=4 Hz (2H$^c$), 7.84 d, d, m $^3J_{H,P}$=13 Hz, $^3J_{H,H}$=8 Hz (2H$^b$), 9.51 s (OH)

$^{13}C$ NMR: 112.6 t, d, q $^1J_{C,F}$=276.6 Hz, $^1J_{C,P}$=136.7 Hz, $^2J_{C,F}$=38.7 Hz (1CF$_2$), 118.8 d, d $^1J_{C,H}$=161 Hz, 1$J_{C,H}$=155 Hz (1C$^f$), 120.0 q, t, d $^1J_{C,F}$=285.9 Hz, $^2J_{C,F}$=31.1 Hz, $^2J_{C,P}$=16.5 Hz (1CF$_3$), 124.9 d, t, m $^1J_{C,P}$=150.8 Hz, $^3J_{C,H}$=7.6 Hz (1C$^a$) 127.6 d, d, d, d, m $^1J_{C,H}$=161.5 Hz, $^3J_{C,P}$=14.7 Hz, $^2J_{C,H}$=5.8 Hz, $^3J_{C,H}$=5.6 Hz (1C$^c$), 134.5 d, d, d, m $^1J_{C,H}$=167.0 Hz, 2$J_{C,P}$=11.1 Hz, $^2J_{C,H}$=6.8 Hz (1C$^b$), 136.6 d, d, d, d, m $^1J_{C,H}$=156.9 Hz, $^3J_{C,H}$=4.4 Hz, $^3J_{C,H}$=4.4 Hz, $^5J_{C,P}$=1.5 Hz (1C$^e$), 144.6 m (1C$^d$)

$^{19}F$ NMR: −80.9 t, d $^3J_{F,F}$=1.8 Hz, $^3J_{F,P}$=1.0 Hz (3F), −127.1 d, q $^2J_{F,P}$=80.0 Hz, $^3J_{F,F}$=1.8 Hz (2F)

$^{31}P$ NMR: 17.5 t, t, t $^2J_{P,F}$=79.9 Hz, $^3J_{P,H}$=12.4 Hz, $^4J_{P,H}$=3.7 Hz (1P).

EXAMPLE 20

Synthesis of bis(pentafluoroethyl)difluoro-3,4,4-trifluorobut-3-en-1-ylphosphorane from bis(pentafluoroethyl)trifluorophosphorane and 3,4,4-trifluorobut-3-en-1-ylmagnesium bromide

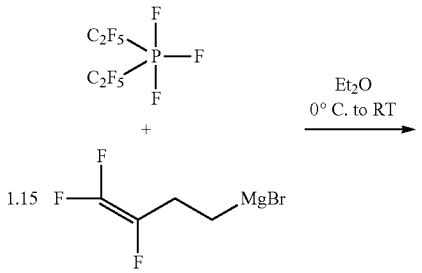

-continued

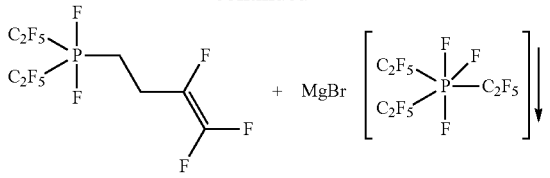

A cold (−50° C.) yellow diethyl ether solution of 3,4,4-trifluorobut-3-en-1-ylmagnesium bromide, $CF_2{=}CFCH_2CH_2MgBr$ (33 mmol in 50 ml, additionally contains 1,1,2,7,8,8-hexafluorocta-1,7-diene and 1,1,2-trifluorobut-1-ene), is reacted with bis(pentafluoroethyl)trifluorophosphorane, $(C_2F_5)_2PF_3$ (9.40 g, 28.8 mmol), in a 100 ml glass round-bottomed flask. A white solid precipitates out. The suspension is stirred at −50° C. to −40° C. for 1 hour. The reaction suspension is subsequently filtered at −30° C., the solid is washed with diethyl ether (5 ml) and subsequently condensed over at RT in vacuo ($10^{-3}$ mbar). Bis(pentafluoroethyl)difluoro-3,4,4-trifluorobut-3-en-1-ylphosphorane, $(C_2F_5)_2(CF_2{=}CFCH_2CH_2)PF_2$ (17.4 mmol), can be isolated as a clear and colourless diethyl ether solution with a yield of 60%.

NMR (lock substance: $CD_3CN$ film; δ in ppm)

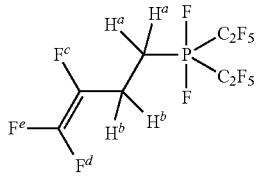

$^1H$-NMR: 2.70 d, d, m $^3J_{H,F}$=20 Hz, $^3J_{H,P}$=18 Hz (2H$^b$), 2.89 d, m $^2J_{H,P}$=18 Hz (2H$^a$).

$^{19}F$-NMR: −49.1 d, t, q, m $^1J_{F,P}$=880 Hz, $^3J_{F,F}$=14 Hz, $^4J_{F,F}$=10 Hz (2F), −82.6 t $^4J_{F,F}$=10 Hz (6F), −105.4 d, d, t, m $^2J_{F,F}$=83 Hz, $^3J_{F,F}$=34 Hz, $^4J_{F,H}$=3 Hz (1F$^e$), −117.4 d, t $^2J_{F,P}$=113 Hz, $^3J_{F,F}$=14 Hz (4F), −123.6 d, d, t, m $^3J_{F,F}$=115 Hz, $^2J_{F,F}$=83 Hz, $^4J_{F,H}$=3 Hz (1F$^d$), −179.3 d, d, t, m $^3J_{F,F}$=115 Hz, $^3J_{F,F}$=34 Hz, $^3J_{F,H}$=20 Hz (1F$^c$).

$^{31}P$-NMR: −31.5 t, qui, t, t $^1J_{P,F}$=880 Hz, $^2J_{P,F}$=113 Hz, $^2J_{P,H}$=18 Hz, $^3J_{P,H}$=18 Hz (1P).

EXAMPLE 21

Synthesis of bis(pentafluoroethyl)-3,4,4-trifluorobut-3-en-1-ylphosphine oxide by Reaction of bis(pentafluoroethyl)difluoro-3,4,4-trifluorobut-3-en-1-ylphosphorane and Hexamethyldisiloxane with Catalytic Amounts of $H_2O$

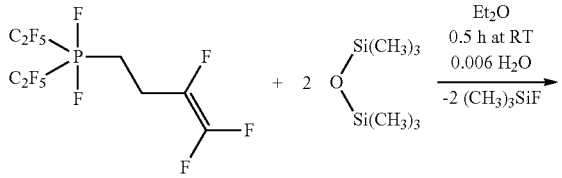

-continued

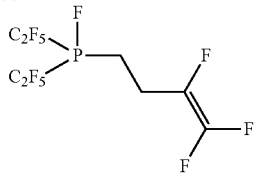

A clear and colourless ether solution with bis(pentafluoroethyl)difluoro-3,4,4-trifluorobut-3-en-1-ylphosphorane, $(C_2F_5)_2(CF_2{=}CFCH_2CH_2)PF_2$ (17.4 mmol, additionally contains 1,1,2,7,8,8-hexafluorocta-1,7-diene and 1,1,2-trifluorobut-1-ene), from Example 1 is stirred with hexamethyldisiloxane, $((CH_3)_3Si)_2O$ (5.75 g, 35.4 mmol), and water (2 mg, 0.11 mmol) at RT for 0.5 hours in a 100 ml glass round-bottomed flask with evolution of gas. The volatile constituents are removed at −40 to −10° C. in vacuo ($10^{-3}$ mbar). Bis(pentafluoroethyl)-3,4,4-trifluorobut-3-en-1-ylphosphine oxide (6.42 g, 16.3 mmol) can be isolated as a pale-yellow liquid with a yield of 94% and a purity of 99%.

NMR (lock substance: $CDCl_3$; δ in ppm)

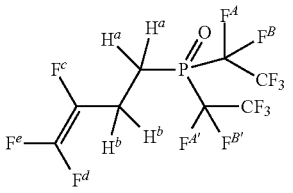

$^1$H-NMR: 2.57 d, t $^2J_{H,P}$=10 Hz, $^3J_{H,H}$=6 Hz (2H$^a$), 2.77 d, d, t, d, d $^3J_{H,F}$=19 Hz, $^3J_{H,P}$=19 Hz, $^3J_{H,H}$=6 Hz, $^4J_{H,F}$=3 Hz, $^4J_{H,F}$=3 Hz (2H$^b$).

$^{13}$C-NMR: 17.5 t, d, m $^1J_{C,H}$=133 Hz, $^2J_{C,P}$=23 Hz (1C$^b$), 20.5 t, d, m $^1J_{C,H}$=132 Hz, $^1J_{C,P}$=62 Hz (1C$^a$), 112.8 d, d, d, q, m $^1J_{C,F_A}$=$^1J_{C,F_B}$=288 Hz, $^1J_{C,F_{A'}}$=$^1J_{C,F_{B'}}$=283 Hz $^1J_{C,P}$=92 Hz, $^2J_{C,F}$=42 Hz (2CF$_2$), 118.3 q, t, d, m $^1J_{C,F}$=286 Hz, $^2J_{C,F}$=30 Hz, $^2J_{C,P}$=17 Hz (2CF$_3$), 126.4 d, d, d, d, t, t $^1J_{C,F}$=234 Hz, $^2J_{C,F}$=54 Hz, $^2J_{C,F}$=18 Hz $^3J_{C,P}$=16 Hz, $^2J_{C,H}$=7 Hz $^3J_{C,H}$=3 Hz (1C$^c$), 153.3 d, d, d, t, d $^1J_{C,F}$=288 Hz, $^1J_{C,F}$=275 Hz, $^2J_{C,F}$=45 Hz, $^3J_{C,H}$=3 Hz, $^4J_{C,P}$=1.3 Hz (1C$^d$).

$^{19}$F-NMR: −80.9 m (6F), −104.3 d, d, t $^2J_{F,F}$=83 Hz, $^3J_{F,F}$=33 Hz, $^4J_{F,H}$=3 Hz (1F$^e$), −122.1 d, m $^2J_{FA,FB}$=340 Hz (2F$_A$), $^2J_{F_A,P}$=79 Hz, $^2J_{FB,P}$=70 Hz, −122.8 d, d, t $^3J_{F,F}$=115 Hz, $^2J_{F,F}$=83 Hz, $^4J_{F,H}$=3 Hz (1F$^d$), −124.2 d, m $^2J_{F_A,F_{B'}}$=342 Hz, $^2J_{FA',P}$=79 Hz, $^2J_{F_{B'},P}$=70 Hz, −179.0 d, d, t, m $^3J_{F,F}$=115 Hz, $^3J_{F,F}$=34 Hz, $^3J_{F,H}$=19 Hz (1F$^c$).

$^{31}$P-NMR: 36.1 t, t, t, t $^2J_{P,F_A}$=$^2J_{P,F_{A'}}$=79 Hz, $^2J_{P,F_B}$=$^2J_{P,F_{B'}}$=70 Hz, $^2J_{P,H}$=19 Hz, $^3J_{P,H}$=10 Hz (1P).

EXAMPLE 22

Synthesis of pentafluoroethyl-3,4,4-trifluorobut-3-en-1-ylphosphinic acid by Hydrolysis of bis(pentafluoroethyl)-3,4,4-trifluorobut-3-en-1-ylphosphine oxide

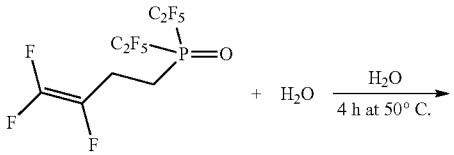

-continued

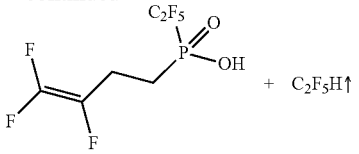

Pale-yellow bis(pentafluoroethyl)-3,4,4-trifluorobut-3-en-1-ylphosphine oxide, $(C_2F_5)_2(CF_2{=}CFCH_2CH_2)P{=}O$ (5.75 g, 14.6 mmol) from Example 2, is emulsified in water (5 ml) in a 25 ml glass round-bottomed flask and warmed (50° C.). The emulsion is stirred at 50° C. for 4 h. All volatile constituents are subsequently removed at RT to 50° C. in vacuo ($10^{-3}$ mbar). Pentafluoroethyl-3,4,4-trifluorobut-3-en-1-ylphosphinic acid (4.12 g, 14.1 mmol) can be isolated as a pale-yellow liquid with a yield 97% and a purity of 99%.

NMR (lock substance: $CDCl_3$; δ in ppm)

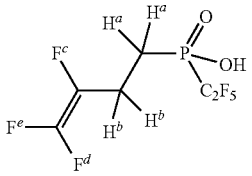

$^1$H-NMR: 2.25 d, t $^2J_{H,P}$=13 Hz, $^3J_{H,H}$=8 Hz (2H$^a$), 2.72 d, d, t, d, d $^3J_{H,F}$=20 Hz, $^3J_{H,P}$=12 Hz, $^3J_{H,H}$=8 Hz, $^4J_{H,F}$=4 Hz, $^4J_{H,F}$=2 Hz (2H$^b$), 13.26 s $\Delta\nu_{1/2}$=2 Hz (1OH).

$^{13}$C-NMR: 17.8 t, d, m $^1J_{C,H}$=133 Hz, $^2J_{C,P}$=23 Hz (1C$^b$), 21.8 t, d, m $^1J_{C,H}$=131 Hz, $^1J_{C,P}$=104 Hz (1C$^a$), 111.1 t, d, q, m $^1J_{C,F}$=277 Hz, $^1J_{C,P}$=133 Hz, $^2J_{C,F}$=40 Hz (CF$_2$), 118.5 q, t, d, m $^1J_{C,F}$=286 Hz, $^2J_{C,F}$=31 Hz, $^2J_{C,P}$=17 Hz (CF$_3$), 126.7 d, d, d, d, m $^1J_{C,F}$=235 Hz, $^2J_{C,F}$=53 Hz, $^2J_{C,F}$=17 Hz $^3J_{C,P}$=16 Hz (1C$^c$), 153.0 d, d, d, t $^1J_{C,F}$=288 Hz, $^1J_{C,F}$=275 Hz, $^2J_{C,F}$=46 Hz, $^3J_{C,H}$=3 Hz (1C$^d$).

$^{19}$F-NMR: −80.7 s $\Delta\nu_{1/2}$=4 Hz (3F), −103.0 d, d, t, m $^2J_{F,F}$=83 Hz, $^3J_{F,F}$=33 Hz, $^4J_{F,H}$=2 Hz (1F$^e$), −121.9 d, d, t $^3J_{F,F}$=115 Hz, $^2J_{F,F}$=83 Hz, $^4J_{F,H}$=4 Hz (1F$^d$), −127.3 d $^2J_{F,P}$=84 Hz (2F), −176.9 d, d, t $^3J_{F,F}$=115 Hz, $^3J_{F,F}$=33 Hz, $^3J_{F,H}$=20 Hz (1F$^c$).

$^{31}$P-NMR: 33.8 t, t, t $^2J_{P,F}$=84 Hz, $^2J_{P,H}$=13 Hz, $^3J_{P,H}$=12 Hz (1P).

EXAMPLE 23

Synthesis of bis(pentafluoroethyl)difluoro-1,2,2-trifluorovinylphosphorane from bis(pentafluoroethyl)trifluorophosphorane and 1,2,2-trifluorovinylzinc chloride

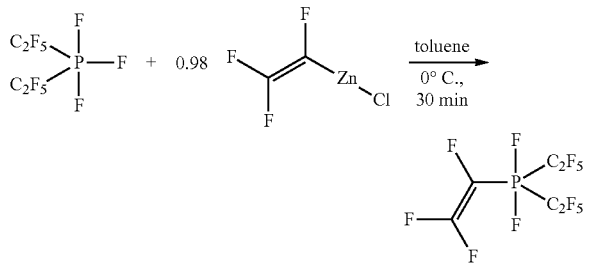

A cold (0° C.) dark-brown solution of trifluorovinylzinc chloride, $CF_2{=}CFZnCl$ (795 mg; 4.37 mmol, additionally contains 1.46 mmol of $Et_2O$ and 2.24 mmol of $C_6H_5CF_3$ as internal standard), in toluene (10 ml) is reacted with bis (pentafluoroethyl)trifluorophosphorane, $(C_2F_5)_2PF_3$ (1.46 g; 4.48 mmol), over the course of 15 min In a 25 ml glass round-bottomed flask. The conversion to $(C_2F_5)_2(CF_2{=}CF)PF_2$ (714 mg; 1.84 mmol) is calculated as 42% with the aid of the internal standard. The brown-black suspension is firstly condensed over at RT and the condensate is subsequently condensed over at −40° C. to −25° C. in vacuo ($10^{-3}$ mbar). The resultant colourless condensate contains the product in toluene (10 ml) and 1.72 mmol of $C_6H_5CF_3$. This clear and colourless liquid is used without further purification.

NMR (lock substance: $CD_3CN$; δ in ppm)

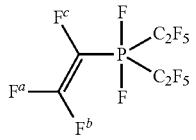

$^{19}$F-NMR: −55.8 d, d, qui, d, hep, d $^1J_{F,P}$=920 Hz, $^4J_{F,F}$=54 Hz, $^3J_{F,F}$=14 Hz, $^4J_{F,F}$=11 Hz, $^4J_{F,F}$=9 Hz, $^3J_{F,F}$=5 Hz (2F), −58.8 d, d, d, t $^3J_{F,F}$=40 Hz, $^3J_{F,P}$=22 Hz, $^2J_{F,F}$=17 Hz, $^4J_{F,F}$=11 Hz (1F$^a$), −81.6 d, t, d, d $^3J_{F,F}$=113 Hz, $^4J_{F,F}$=54 Hz, $^2J_{F,F}$=17 Hz, $^3J_{F,P}$=16 Hz (1F$^b$), −82.4 t $^4J_{F,F}$=9 Hz (6F), −117.2 d, t $^2J_{F,P}$=120 Hz, $^3J_{F,F}$=14 Hz (4F), −185.5 d, d, d, t $^3J_{F,F}$=113 Hz, $^2J_{F,P}$=83 Hz, $^3J_{F,F}$=40 Hz, $^3J_{F,F}$=5 Hz (1F$^c$).

$^{31}$P-NMR: −54.1 t, qui, d, d, d $^1J_{P,F}$=920 Hz, $^2J_{P,F}$=120 Hz, $^2J_{P,F}$=83 Hz, $^3J_{P,F}$=22 Hz, $^3J_{P,F}$=16 Hz (1P).

EXAMPLE 24

Synthesis of bis(pentafluoroethyl)(1,2,2-trifluorovinyl)-phosphine oxide from bis(pentafluoroethyl) difluoro-1,2,2-trifluorovinylphosphorane and Hexamethyldisiloxane

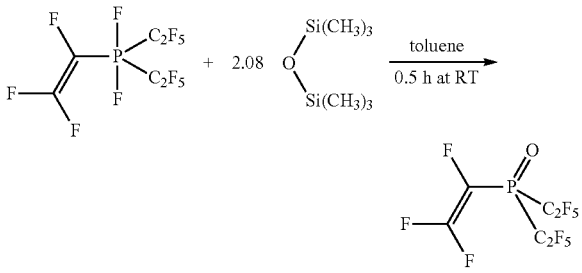

A colourless solution of bis(pentafluoroethyl)difluorotrifluorovinylphosphorane, $(C_2F_5)_2(CF_2{=}CF)PF_2$(714 mg; 1.84 mmol), in toluene (10 ml, contains 1.72 mmol of $C_6H_5CF_3$ as internal standard) from Example 4 is reacted with hexamethyldisiloxane, $((CH_3)_3Si)_2O$ (620 mg; 3.82 mmol) in a 25 ml glass round-bottomed flask. The reaction solution is stirred at RT for 30 min. After 30 min at RT, the conversion is quantitative. The amount of bis(pentafluoroethyl)trifluorovinylphosphine oxide (655 mg, 1.79 mmol) is determined with the aid of the internal standard, and the solution is used without further purification.

NMR (lock substance: $CD_3CN$; δ in ppm)

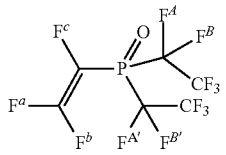

$^{19}$F-NMR: −63.6 d, d, d $^3J_{F,F}$=29 Hz, $^3J_{F,P}$=11 Hz (1F$^a$), $2J_{F,F}$=7 Hz, −80.4 s $\Delta v_{1/2}$=6 Hz (6F), −93.7 d, d, d $^3J_{F,F}$=121 Hz, $^3J_{F,P}$=15 Hz, $^2J_{F,F}$=7 Hz (1F$^b$), −121.1 d, m $^2J_{F_A,F_B}$=327 Hz, $^2J_{F_A,P}$=$^2J_{F_B,P}$=83 Hz (2F$_A$), −122.9 d, m $^2J_{F_A,F_{B'}}$=340 Hz, $^2J_{F_A,P}$=$^2J_{F_{B'},P}$=83 Hz (2F$_B$), −199.4 d, d, d $^3J_{F,F}$=121 Hz, $^2J_{F,P}$=44 Hz, $^3J_{F,F}$=29 Hz (1F$^c$).

$^{31}$P-NMR: 7.7 t, t, d, d, d $^2J_{P,F_A}$=$^2J_{P,F_B}$=83 Hz, $^2J_{P,F_{A'}}$=$^2J_{P,F_{B'}}$=83 Hz, $^2J_{P,F}$=44 Hz, $^3J_{P,F}$=15 Hz, $^3J_{P,F}$=11 Hz (1P).

EXAMPLE 25

Synthesis of pentafluoroethyl-1,2,2-trifluorovinylphosphinic acid from bis(pentafluoroethyl)(1,2,2-trifluorovinyl)phosphine oxide and Water

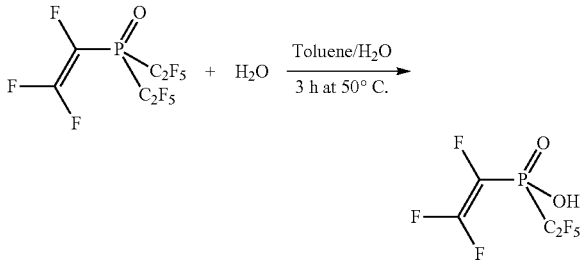

A colourless solution of bis(pentafluoroethyl)trifluorovinylphosphine oxide, $(C_2F_5)_2(CF_2{=}CF)P{=}O$(655 mg, 1.79 mmol), in toluene (10 ml, also contains $C_6H_5CF_3$, $((CH_3)_3Si)_2O$ and $(CH_3)_3SiF$) is emulsified in water (15 ml) in a 25 ml glass round-bottomed flask and warmed (50° C.). The emulsion is stirred at 50° C. for 3 h. After 3 h at RT, the conversion is quantitative. All volatile constituents are removed at RT in vacuo ($10^{-3}$ mbar). Pentafluoroethyltrifluorovinylphosphinic acid (410 mg, 1.76 mmol) can be isolated as a colourless liquid with the yield of 98%.

NMR (solvent: $CD_3CN$; δ in ppm)

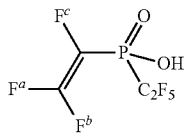

$^1$H-NMR: 13.00 s $\Delta v_{1/2}$=7 Hz (1OH)

$^{19}$F-NMR: −75.9 d, d, d $^3J_{F,F}$=30 Hz, $^2J_{F,F}$=24 Hz, $^3J_{F,P}$=15 Hz (1F$^a$), −81.9 s $\Delta v_{1/2}$=6 Hz (3F), −97.4 d, d, d $^3J_{F,F}$=120 Hz, $^2J_{F,F}$=24 Hz, $^3J_{F,P}$=15 Hz (1F$^b$), −128.9 d $^2J_{F,R}$=90 Hz (2F), −195.0 d, d, d $^3J_{F,F}$=120 Hz, $^2J_{F,P}$=65 Hz, $^3J_{F,F}$=30 Hz (1F$^c$)

$^{31}$P-NMR: 0.6 t, d, d, d $^2J_{P,F}$=90 Hz, $^2J_{P,F}$=65 Hz, $^3J_{P,F}$=15 Hz, $^3J_{P,F}$=15 Hz (1P).

EXAMPLE 26

Polymerisation of pentafluoroethyl-(4-styryl)phosphinic acid with AIBN

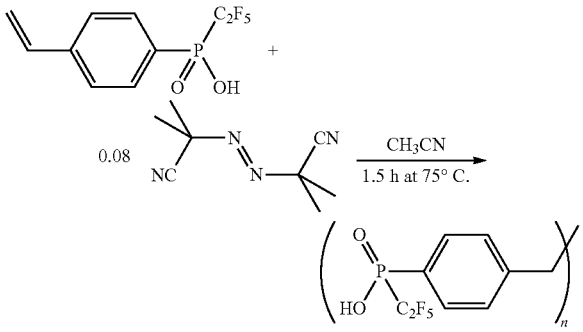

Pentafluoroethyl-(4-styryl)phosphinic acid, $(C_2F_5)$(4-styryl)P(O)OH·0.5$H_2O$ (1.12 g; 3.79 mmol) is dissolved in $CH_3CN$ (20 ml) with azobisisobutyronitrile (AIBN)(50 mg; 0.30 mmol) in a 25 ml glass round-bottomed flask with vigorous stirring and warmed (75° C.). Cloudiness can immediately be observed. After 1.5 h at 75° C., the milky-cloudy suspension is transferred into a 100 ml glass round-bottomed flask with $CH_3CN$ (5 ml). All volatile substances are removed at RT in vacuo ($10^{-3}$ mbar), and the white pulverulent solid is dried for a further 2 h. Polymeric material can be isolated as a white powder with a yield of 96%. The polymer also contains 0.3 equivalent of $CH_3CN$ and 0.1 equivalent of $H_2O$ (elemental analysis) and also about 5 mol % of unpolymerised $(C_2F_5)$(4-styryl)P(O)OH (NMR). The average degree of polymerisation (351600 formula units) was determined via the weight average molecular weight and the polydispersity by means of GPC.

Impurities, such as $CH_3CN$, can be removed on drying (50-60° C.) in a high vacuum for 1 day.

Analytical Result (GPC):

| | Mw | Mp | D |
|---|---|---|---|
| Poly(pentafluoroethyl-4-styrylphosphinic acid) | 94,522,300 | 5,143,990 | 4,338.20 |
| | 100,648,000 | 5,179,390 | 2,905.77 |

Notes:
entire polymer distribution evaluated

| | Mw | Mp | D |
|---|---|---|---|
| Poly(pentafluoroethyl-4-styrylphosphinic acid) | 17,487,700 | 5,143,990 | 2.92 |
| | 17,387,700 | 5,179,390 | 2.80 |

Notes:
only maximum evaluated

Mw is the weight average molecular weight, calculated over the entire peak.

Mp is the molecular weight at the peak maximum.

D (polydispersity) is an indication of the width of the weight distribution of the peak. The higher this value, the broader the weight distribution.

The analysis shows a very broad weight distribution with a maxima at ~5,200,000 Da.

The following experiment demonstrates the applicability thereof.

Determination of the Ion Exchange Capacity (IEC):

The polymer $[(C_2F_5)$(4-styryl)P(O)OH$]_n$ (214 mg; 0.748 mmol) is suspended in 0.1 M $NaOH_{(aq)}$ (10 ml, titre: 1.0019) in a glass round-bottomed flask (25 ml) and stirred vigourously at RT for 24 h. The resultant solution is titrated with 0.1 M $HCl_{(aq)}$ (titre: 1.0185). The consumption of 0.1 M $HCl_{(aq)}$ at the equivalence point is 2.752 ml. Taking into account the titre, this results in an amount of 0.720 mmol of acidic protons in the polymeric material. A value of 3.36 meq/g (theor.: 3.49 meq/g) thus arises for the IEC. Taking into account the impurities, such as $CH_3CN$, the measured ion exchange capacity IEC of the polymer is >99% of the theoretical value.

EXAMPLE 27

Extraction of Europium Chloride using polypentafluoroethyl-4-styrylphosphinic acid

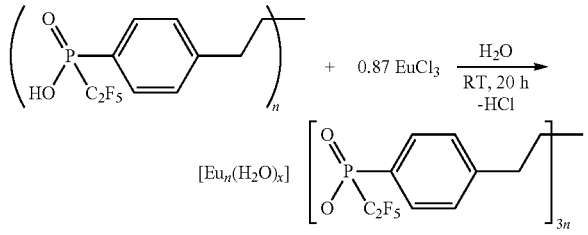

Polypentafluoroethyl-4-styrylphosphinic acid, $[(C_2F_5)$(4-styryl)-P(O)OH·0.5$H_2O]_n$ (210 mg; 0.712 mmol), is added to a solution of $EuCl_3$ (159 mg; 0.616 mmol) in $H_2O$ (2 ml) in an FEP reactor ($Ø_i$=8 mm), and the mixture is stirred at RT. After 20 h, the pale-yellow suspension with fine precipitate (A) is centrifuged, the mother liquor is decanted and the white solid (A) is washed with $H_2O$ (3×2 ml). The combined mother liquors are evaporated at RT in vacuo ($10^{-3}$ mbar), and the resultant white and solid residue (B) (157 mg) is dried at RT in vacuo ($10^{-3}$ mbar) for a further 5 h. The white solid (B) fluoresced intensely red ($EuCl_3$) on irradiation with UV light (λ=366 nm). The water content of the solid was determined as 45 mg (2.5 mmol) by means of Karl Fischer titration. Elemental analysis of the solid shows little contamination by $CH_3CN$ (3 mg; 0.07 mmol) from the starting material. No chloride was detected in the polymer (A) by X-ray fluorescence analysis. The ratio of europium to phosphorus is 0.30 to 1.00. $EuCl_3$ (157 mg−45 mg ($H_2O$)−3 mg ($CH_3CN$)=109 mg (0.422 mmol)) can be recovered as white solid (A). $Eu^{3+}$ (0.194 mmol) in the polymer are replaced by $H^+$. The ratio of europium to phosphorus is thus 0.272 to 1.00, which corresponds to replacement of 82% of the acidic protons in the polymer (A). On irradiation with UV light at λ=366 nm, the polymer exhibits a pale orange fluorescence, whereas it fluoresces intensely pink at λ=254 nm. A quantum yield of 3.6% is determined with the aid of fluorescence spectroscopy. Excitation at λ=250.0 nm causes maximum absorption with emission maxima at λ=590.0 nm ($\Delta v_{1/2}$=9.8 nm) and 610.5 nm ($\Delta v_{1/2}$=9.7 nm).

EXAMPLE 28

Extraction of Terbium Chloride using polypentafluoroethyl-4-styrylphosphinic acid

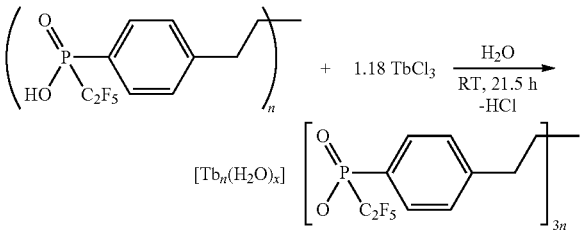

Polypentafluoroethyl-4-styrylphosphinic acid, $[(C_2F_5)(4\text{-styryl})P(O)OH\cdot 0.5H_2O]_n$ (52 mg; 0.176 mmol), is added to a solution of $TbCl_3$ (55 mg; 0.207 mmol) in $H_2O$ (1 ml) in an FEP reactor ($Ø_i$=8 mm), and the mixture is stirred at RT. After 22 h, the white suspension with bulky precipitate (A) is centrifuged, the mother liquor is decanted and the white solid (A) is washed with $H_2O$ (2×1 ml). The combined mother liquors are evaporated at RT in vacuo ($10^{-3}$ mbar), and the resultant white and solid residue (B) (62 mg) is dried at RT in vacuo ($10^{-3}$ mbar) for a further 2 h. The white solid (B) fluoresced yellow-green ($TbCl_3$) on irradiation with UV light (λ=254 nm). Analogously to the experiment with europium (Example 6), the residue here can again be assumed to be a hexaaqua complex, $[Tb(H_2O)_6]Cl_3$. The water content is estimated as 18 mg (1.0 mmol). Elemental analysis of the solid shows little contamination by $CH_3CN$ (1 mg; 0.02 mmol) from the starting material. No chloride was detected in the polymer (A) by X-ray fluorescence analysis. The ratio of terbium to phosphorus is 0.33 to 1.00. $TbCl_3$ (62 mg−18 mg ($H_2O$)−1 mg ($CH_3CN$)=43 mg (0.162 mmol)) can be isolated as white solid (A). $Tb^{3+}$ (0.045 mmol) in the polymer are replaced by $H^+$. The ratio of terbium to phosphorus is thus 0.26 to 1.00, which corresponds to replacement of 77% of the acidic protons in the polymer (A). On irradiation with UV light at λ=254 nm, the polymer (A) likewise fluoresces yellow-green.

EXAMPLE 29

Graft Polymerisation of $(C_2F_5)(CH_2{=}CHCH_2CH_2)P(O)OH$ on a Porous Polymer Support (Hydrophilic Crosslinked Polyvinyl Ether) using $[NH_4]_2$cerium $[NO_3]_6$ in $H_2O$ at 40° C.

White and solid polymer gel (~20 g) (filtered out of $H_2O$ suspension) is initially introduced in a 500 ml 3-necked round-bottomed flask with reflux condenser, dropping funnel and precision glass stirrer, and an aqueous $(C_2F_5)(CH_2{=}CHCH_2CH_2)P(O)OH$ solution (18.77 g in 100 ml of water) is added. As initiator, an aqueous $[NH_4]_2$cerium $[NO_3]_6$ (2.41 g)/$HNO_3$ (65%, 1.44 g) solution (20 ml) is placed in the dropping funnel. The entire apparatus is degassed in a membrane-pump vacuum (100 mbar) and flooded with $N_2$. The reaction suspension is warmed (40° C.) and the initiator substance is subsequently added. The now-yellow suspension is stirred at 40° C. for 22 h. The mixture is subsequently filtered, and the filter cake is washed with water (2×100 ml). The pale-yellow polymer material is washed with water (3×100 ml) and an $H_2SO_4$ (concentrated, 25 g)/ascorbic acid (17.6 g) solution (500 ml)(5×100 ml). The mixture is subsequently washed neutral several times more with an $NaHPO_4$/NaOH buffer solution (pH 7, 50 mM) and water (in total 1000 ml). The slightly beige-coloured polymer material is stored in the refrigerator at 0° C. under Millipur water. A polymer material forms in which 0.9 g of the phosphinic acid employed is bonded to 1 g of polymer.

The polymer material obtained is in addition investigated by solid-state and liquid NMR spectroscopy. The signals detected are comparable with those of but-3-en-1-ylpentafluoroethylphosphinic acid and can be assigned to the structural unit

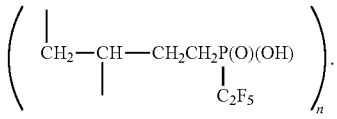

EXAMPLE 30

Polymerisation in the Presence of a Silica-Gel Support Material

Step 1: Preparation of Mercapto-Silica Gel

Object: Synthesis of LiChroprep Mercapto from LiChroprep Si 100; 15 μm-25 μm. LiChroprep Si 100 as an average pore size of 10 nm.

LiChroprep Si 100 is a traditionally prepared irregular $SiO_2$ sorbent (silica gel) having an average pore size of 10 nm and an average particle size of 15 μm to 25 μm. LiChroprep Si is merely a trade name. Silica gels of this type are prepared in accordance with the prior art and are known to the person skilled in the art.

Equipment: 1l 3-necked flask, precision glass stirrer, reflux condenser, oil-bath heating 90° C., nitrogen feed, 50 ml dropping funnel, 1× stirrer, 2× glass suction filters 1l Por. 4

1×2000 ml three-necked flask, 2×2l suction bottle, 1× porcelain dish

TABLE 1

Chemicals used:

| Amount | Chemical | Art. No. | Batch | Property |
|---|---|---|---|---|
| 100.1 g | LiChroprep Si 100 (15-25 μm) | | F553395 | $S_{BET}$ = 282.2 $m^2/g$ |
| 4.1086 g | Sodium acetate | 1.06268 | A0472968 322 | 0.1M |
| 43.1 g | Mercapto- | AB111217 | 1068410 | 180.34 |
| 43.1 ml | propylmethyl-dimethoxysilane w = 95% | ABCR | | g/mol |
| | Dist. water | — | — | |
| 1.3 l | Methanol | 1.06009.5000 | I734309416 | |

Procedure:

100.1 g of LiChroprep Si100 are initially introduced in a 1000 ml three-necked flask and suspended in 0.1 molar sodium acetate solution at 250 rpm.

The mercaptopropylmethyldimethoxysilane should be added dropwise over the course of 10 to 15 minutes with stirring.

The suspension is heated under reflux (90° C.) for 3 hours.

After heating for 3 hours, the suspension is slowly cooled to room temperature with stirring.

The gel is then filtered off with suction on a 1 l Por4 frit, suspended again with 1 l of deionised water and filtered off with suction. The gel is transferred into a 2 l three-necked flask, and 1 l of methanol is added. The suspension is heated at 65-69° C. for 30 minutes. After cooling to room temperature, the reaction mixture is filtered off with suction on a 1 l Por4 frit, rinsed twice with 100 ml of methanol and dried over vacuum for 1 hour. The product is left to stand overnight in the fume hood without vacuum and next day dried again for 3 hours in vacuo.

Elemental analysis: C=6.3%, S=4.0%

2nd Step Addition of but-3-en-1-yl(pentafluoroethyl) phosphinic acid

Product batch: ScW14FE002

Equipment:

2×250 ml three-necked flasks
condenser
precision glass stirrer and stirrer sleeve
hotplate
thermometer and oil bath
1000 µl Eppendorf pipette equi No.: 70221348
analytical balance equ No.: 70081915
125 ml Por.4 frit

TABLE 2

Chemicals:

| Chemical | Article number/batch | Molar amount | Equivalence milimol | Weight/ volume |
|---|---|---|---|---|
| Mercapto-silica gel | ScW14FE001 | 1.2699 mmol/g 5.77 mmol | 4.5 µmol/m² | 4.4990 g |
| But-3-en-1-yl-(pentafluoro-ethyl)phosphinic acid | | 13.71 mmol | 2.4 | 3.2562 g |
| Glacial acetic acid | K28057163032 1.00063.1000 | 9 mmol | 2 mmol/g of silica | 0.540 g 0.515 ml |
| V65 | | 1.1142 mmol | 20% mol | 0.2836 g |
| Methanol | I734309416 1.06009.5000 | | | 90 ml |

Procedure:

The mercapto-silica gel (ScW14FE001) was initially introduced in a three-necked flask with 40 ml of methanol and suspended under nitrogen. The 3-butenylpentafluoroethylphosphinic acid, the glacial acetic acid and the V65 were then added. The vessels in which the weighed amounts were located were rinsed twice with a small amount of methanol. The reaction mixture was boiled at a bath temperature of 67° C. for 6h under nitrogen. The lukewarm reaction solution was filtered off with suction via a 125 ml Por.4 frit.

The gel was transferred into another 250 ml three-necked flask, boiled with about 50 ml of methanol for 5 min with stirring and filtered off with suction. This washing step was repeated 3 times.

The gel was dried firstly in a fume hood overnight and then at 30° C. in a vacuum drying cabinet for 16 hours.

Elemental analysis:

3. Determination of the Terbium Chloride Binding Capacity

Equipment:

10, 25 and 100 ml volumetric flasks
Ultrospec 4000 UV spectrometer, Pharmacia Biotech, Inv. No. 59485
ultrasound bath
Sartorius BP221 F analytical balance Equ Nr:70098279
Eppendorf 5804 centrifuge, Equ No.: EM 2363

TABLE 3 chemicals used

| Chemical | Article number/ batch | Molecular weight or $S_{BET}$ |
|---|---|---|
| Terbium chloride hexahydrate (TbCl3*6 H2O) | 1315353 | 265.29 |
| LiChroprep Si 100, 15-25 µm | F553395 | |
| Mercapto-silica gel | ScW14FE001 | |
| Silica gel from step 2 | ScW14FE002 | |
| Water, MilliQ | | |

A calibration curve of the adsorption of terbium chloride hexahydrate in water at 220 nm in the range from 0.018 to 1.832 mg/ml is recorded. The line of best fit followed the line equation y=0.8502 x+0.009 where $R^2$=0.999.

In each case 10 ml of a stock solution of 0.521 mg of $TbCl_3$*6 $H_2O$ in water are added to about 200 mg (weighed precisely) of the respective silica gel, as indicated in Table 4, in a sealed glass vessel and left in the ultrasound bath in parallel for 10 min. In each case 5 ml of the solution are subsequently centrifuged at 5000 rpm for 5 min and the adsorption of the supernatant at 220 nm is measured.

TABLE 4

Results:

| Sample | Adsorption (220 nm) of the supernatant |
|---|---|
| Stock solution (0.521 mg of $TbCl_3$*6 $H_2O$ in water) | 0.437 |
| Silica gel LiChroprep Si 100, 15-25 µm | 0.401 |
| Silica gel from step 2 | 0.148 |

Measurement of the $TbCl_3$ adsorption shows a decrease of 70%, which corresponds to the amount of Tb cations bound.

The invention claimed is:

1. A compound of the formula I

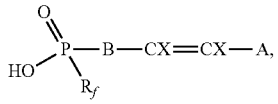

I where $R_f$ denotes a straight-chain or branched perfluoroalkyl group having 1 to 12 C atoms, A denotes H, F, Cl or a straight-chain or branched alkyl group having 1 to 12 C atoms, B denotes $—(CR_1R_2)_n—$, $[—(CR_1R_2)_m—O—(CR_1R_2)_{m1}—]_{m2}$, arylene or substituted arylene, X denotes H, F and/or Cl, n denotes an integer from 0 to 20, m denotes an integer from 1 to 20, $m_1$ denotes an integer from 0 to 8, $m_2$ denotes an integer from 1 to 20 and $R_1$ or $R_2$ each, independently of one another, denote H, F, Cl or a straight-chain or branched alkyl group having 1 to 12 C atoms.

2. A compound according to claim 1, wherein $R_f$ denotes a straight-chain or branched perfluoroalkyl group having 1 to 8 C atoms.

3. A compound according to claim 1, wherein A and X are identical.

4. A compound according to claim 1, wherein B denotes $—(CR_1R_2)_n—$, arylene or substituted arylene.

5. A process for the preparation of a compound of the formula I according to claim 1, which comprises:

a) hydrolysing a compound of the formula II $$(F)_x(R_f)_{4-x}P—B—CX{=}CX\text{-}A \qquad \text{II},$$

where $R_f$, A, B and X have a meaning indicated in claim 1 and x denotes 2, to give an intermediate compound of the formula IIIa, IIIa

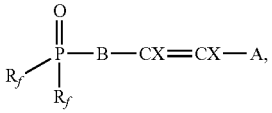

where $R_f$, A, B and X have a meaning indicated in formula II, or b) reacting a compound of the formula II $$(F)_x(R_f)_{4-x}P—B—CX{=}CX\text{-}A \qquad \text{II},$$

where $R_f$, A, B and X have a meaning indicated in claim 1 and x denotes 2 or 3, with a hexaalkyldisiloxane optionally in the presence of a catalytic amount of water, where the alkyl groups of the hexaalkyldisiloxane each, independently of one another, denote a straight-chain or branched alkyl group having 1 to 4 C atoms, to give an intermediate compound of the formula III,

III

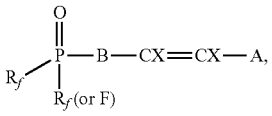

where $R_f$, A, B and X a have a meaning indicated in formula II; and then hydrolysing the intermediate compound of formula IIIa or III to obtain a compound of formula I.

6. A compound of the formula IIIa,

IIIa

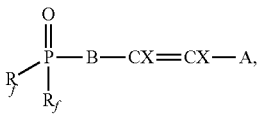

where $R_f$ denotes a straight-chain or branched perfluoroalkyl group having 1 to 12 C atoms, A denotes H, F, Cl or a straight-chain or branched alkyl group having 1 to 12 C atoms, B denotes $—(CR_1R_2)_n—$, $[—(CR_1R_2)_m—O—(CR_1R_2)_{m1}—]_{m2}$, arylene or substituted arylene, X denotes H, F and/or Cl, n denotes an integer from 0 to 20, m denotes an integer from 1 to 20, $m_1$ denotes an integer from 0 to 8, $m_2$ denotes an integer from 1 to 20 and $R_1$ or $R_2$ each, independently of one another, denote H, F, Cl or a straight-chain or branched alkyl group having 1 to 12 C atoms.

7. A method for the preparation of oligomers or polymers which comprises oligomerizing or polymerizing a compound of claim 1.

8. Oligomer or polymer containing polymerised compounds of the formula I, according to claim 1, as monomer units.

9. A process for the preparation of oligomers or polymers according to claim 8, comprising polymerizing a compound of the formula I, optionally together with further monomers and optionally in the presence of a crosslinking agent.

10. Process according to claim 9, wherein the polymerisation is carried out by means of free radicals.

11. Process according to claim 9 wherein a homo-polymer is prepared.

12. Process according to claim 9 wherein the polymerisation is carried out without crosslinking agents.

13. Process according to claim 9 wherein the polymerisation is carried out in, on or at a support material.

14. Composite material comprising a support material and at least one compound according to claim 1.

15. An ion exchanger or a Brønsted acid catalyst material comprising a compound of claim 1 or a polymer or oligomer of a compound of claim 1.

16. A method for the extraction of cations of the rare earths from a solution which comprises contacting the solution with a material comprising a compound of claim 1 or a polymer or oligomer thereof.

17. A salt corresponding to the formula IV,

IV

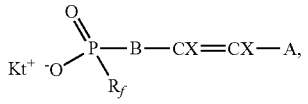

where the cation $Kt^+$ in formula IV denotes an inorganic or organic cation and where $R_f$ denotes a straight-chain or branched perfluoroalkyl group having 1 to 12 C atoms, A denotes H, F, Cl or a straight-chain or branched alkyl group having 1 to 12 C atoms, B denotes $—(CR_1R_2)_n—$, $[—(CR_1R_2)_m—O—(CR_1R_2)_{m1}—]_{m2}$, arylene or substituted arylene, X denotes H, F and/or Cl, n denotes an integer from 0 to 20, m denotes an integer from 1 to 20, $m_1$ denotes an integer from 0 to 8, $m_2$ denotes an integer from 1 to 20 and $R_1$ or $R_2$ each, independently of one another, denote H, F, Cl or a straight-chain or branched alkyl group having 1 to 12 C atoms.

18. A polymer or oligomer comprising polymerized units of a salt of claim 17 as monomer units.

19. Composite material comprising a support material and at least one polymer or oligomer of claim 8.

*20. Composite material comprising a support material and at least one polymer or oligomer of claim 18.*

* * * * *